(12) United States Patent
Dunn et al.

(10) Patent No.: US 10,281,399 B2
(45) Date of Patent: May 7, 2019

(54) SYSTEMS AND METHODS FOR PARTICLE TRACKING USING SPATIOTEMPORAL OFFSET LIGHT BEAMS

(71) Applicant: Board of Regents, The University of Texas System, Austin, TX (US)

(72) Inventors: Andrew Dunn, Austin, TX (US); Hsin-Chih Yeh, Austin, TX (US); Evan Perillo, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/548,861

(22) PCT Filed: Feb. 5, 2015

(86) PCT No.: PCT/US2015/014559
§ 371 (c)(1),
(2) Date: Aug. 4, 2017

(87) PCT Pub. No.: WO2016/126250
PCT Pub. Date: Aug. 11, 2016

(65) Prior Publication Data
US 2018/0031479 A1    Feb. 1, 2018

(51) Int. Cl.
*G01J 1/58*    (2006.01)
*G01N 21/64*    (2006.01)
*G01N 15/14*    (2006.01)

(52) U.S. Cl.
CPC ..... *G01N 21/6428* (2013.01); *G01N 21/6408* (2013.01); *G01N 21/6456* (2013.01); *G01N 15/1434* (2013.01); *G01N 2021/6439* (2013.01)

(58) Field of Classification Search
CPC .............. G01N 21/64; G01N 21/6402; G01N 21/6404; G01N 21/6408; G01N 21/6428
See application file for complete search history.

(56) References Cited

U.S. PATENT DOCUMENTS

| 7,365,344 B2 * | 4/2008 | Aoki | G01N 21/6408 |
| | | | 250/458.1 |
| 7,714,301 B2 | 5/2010 | Jackson et al. | |
| 2011/0267663 A1* | 11/2011 | Murayama | G03H 1/08 |
| | | | 359/9 |

OTHER PUBLICATIONS

Field et al. "Differential Multiphoton Laser Scanning Microscopy", IEEE Journal of Selected Topics in Quantum Electronics, vol. 18, No. 1, Jan.-Feb. 2012, p. 14-28.*
Liu et al. "3D single-molecule tracking using one- and two-photon excitation microscopy", Proc. Of SPIE vol. 8950, 2014, p. 89501C-1-89501C-9.*

(Continued)

*Primary Examiner* — David Porta
*Assistant Examiner* — Mamadou Faye
(74) *Attorney, Agent, or Firm* — Parker Highlander PLLC

(57) ABSTRACT

Systems and methods for particle tracking using spatiotemporal offset light beams. In exemplary embodiments, the optical systems and methods can be used with conventional two-photon microscopy equipment to perform high speed, high precision, and deep tissue three-dimensional single-particle tracking. Exemplary embodiments can be configured for single-molecule studies of biological diffusion and transport processes.

6 Claims, 42 Drawing Sheets

(56) References Cited

OTHER PUBLICATIONS

Field, Jeffrey J., et al. "Differential multiphoton laser-scanning microscopy." *IEEE J Sel Top Quantum Electron* 18 (2012): 14-28.
International Preliminary Report on Patentability issued in International Application No. PCT/US2015/014559, dated Aug. 17, 2017.
International Search Report and Written Opinion issued in International Application No. PCT/US2015/014559, dated May 14, 2015.
Liu, Cong, et al. "3D single-molecule tracking using one-and two-photon excitation microscopy." *Single Molecule Spectroscopy and Superresolution Imaging VII*. vol. 8950. International Society for Optics and Photonics, 2014.

* cited by examiner

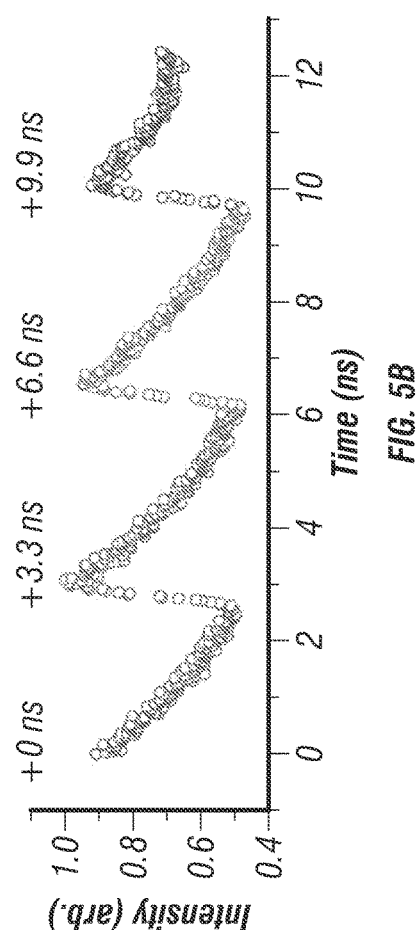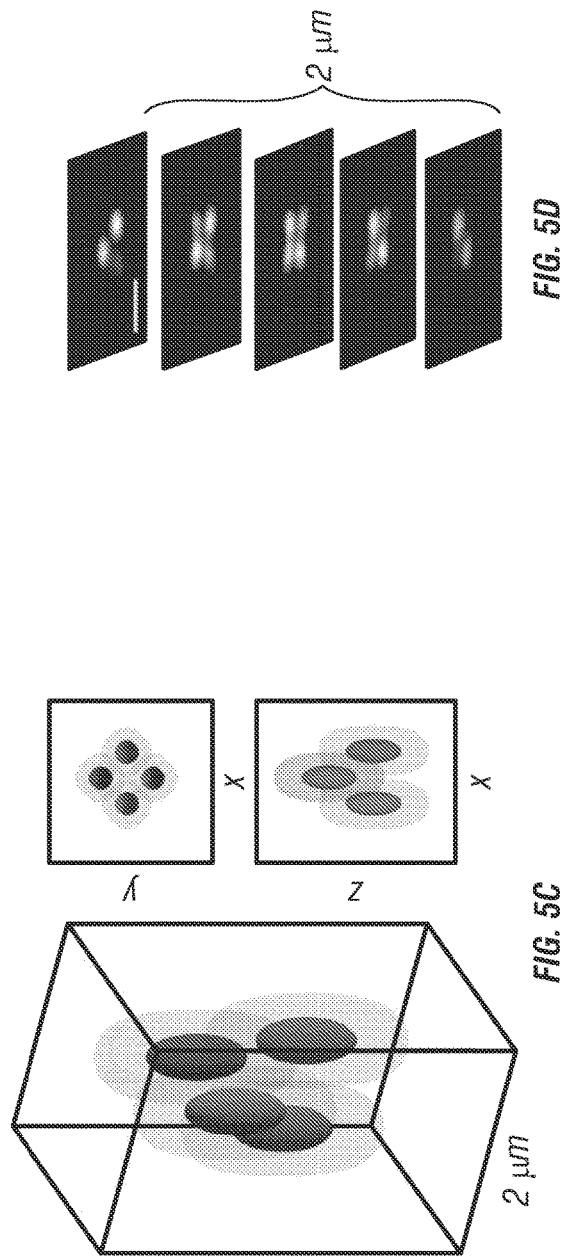

| Depth (μm) | Power per beam (mW) | X localization (nm) | Y localization (nm) | Z localization (nm) |
|---|---|---|---|---|
| 10 | 1.1 | 16.3 | 14.2 | 60.8 |
| 100 | 5.0 | 17.5 | 14.5 | 89.9 |
| 200 | 8.7 | 21.0 | 14.1 | 89.6 |

1P-1E-4D Design

Molecular Detection Function (MDF) = Excitation Volume X Collection Efficiency Function (CEF)

TSUNAMI

Molecular Detection Function (MDF) = Excitation Volume X Collection Efficiency Function (CEF)

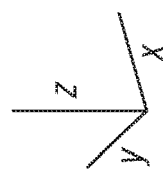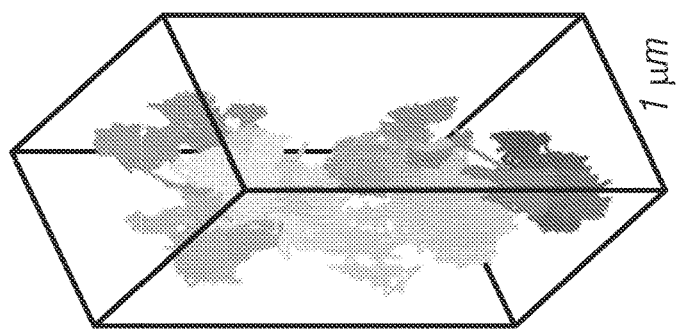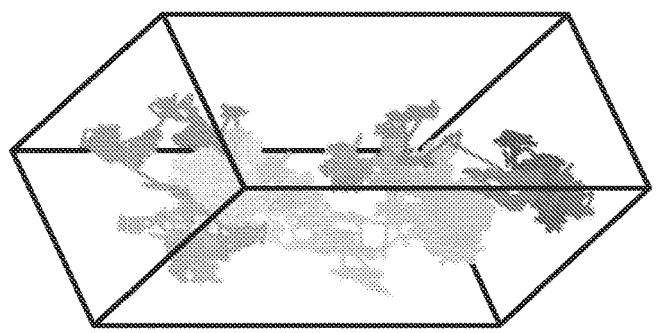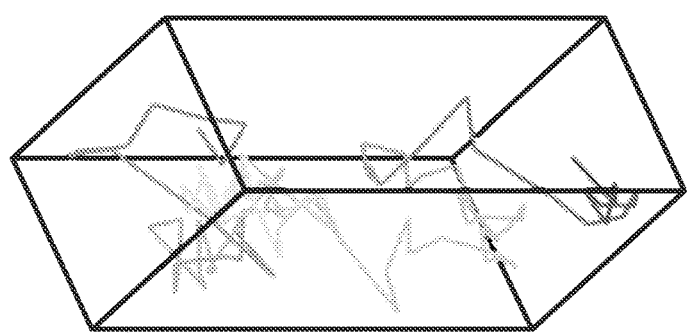
FIG. 11C  FIG. 11D  FIG. 11E $\frac{(G_2 - G_1)}{(G_2 + G_1)}$ $\frac{(G_4 - G_3)}{(G_4 + G_3)}$

SYSTEMS AND METHODS FOR PARTICLE TRACKING USING SPATIOTEMPORAL OFFSET LIGHT BEAMS

GOVERNMENT LICENSE RIGHTS

This invention was made with government support under Grant Nos. R01 EB008715, EB011556, NS078791, NS082518 and R21 CA193038 awarded by the National Institutes of Health. The government has certain rights in the invention.

This application is a national phase application under 35 U.S.C. § 371 of International Application No. PCT/US2015/014559, filed Feb. 5, 2015. The entire contents of the above-referenced disclosure is specifically incorporated herein by reference without disclaimer.

BACKGROUND INFORMATION

Single-particle tracking (SPT) has enabled the direct observation of dynamic behaviors of particles (as used herein, a particle can be a single biomolecule, a molecular complex, a vesicle, a lipid granule, or a viral capsid) inside complex biological systems [1], with particle localization precision better than the diffraction limit of light [2,3]. Through trajectory analysis SPT has provided insight into motor protein kinetics [4,5] cellular membrane dynamics, [6-8] mRNA transport [9,10] and virus internalization processes [11,12]. As the basis of passive micro rheology, SPT has also shed light on the local environments of tracked particles through the observation of changes in particles' random movements [13].

Whereas SPT is becoming a powerful research tool, all current techniques suffer from one or more of the following problems: shallow penetration depth (arising from the use of one-photon excitation) [14-16], limited ztracking range (e.g. TIRF microscopy), poor temporal resolution (e.g. frame-by-frame analysis in camera-based methods) [17,18], and low information content (e.g. no information on the fluorescence lifetime) [19]. As two-photon (2P) microscopy has become a standard method for deep tissue imaging [20] a few reports demonstrated 3D tracking based on two-photon excitation. The first approach used a circular scanning pattern of the focused laser beam to track particles [2, 21] but was limited to a temporal resolution of 20~32 ms due to the laser scanning and signal demodulation. More recently, 3D tracking of gold nanorods with 2P excitation was demonstrated by exciting multiple foci and detecting fluorescence with an EM-CCD [18] but the 3D temporal resolution was limited to about 0.5 s. Moreover, the use of a camera in multifocal 2P laser scanning microscopy (2P-LSM) limits the working depth of SPT in scattering samples [22]. Although SPT with superior temporal resolution (bounded mainly by the emission rate of the fluorescent label) and simultaneous fluorescence lifetime measurements have been achieved using confocal setups with 3-5 single-element/photon-counting detectors (PMTs or APDs) for spatial filtering [14-16], these methods not only have limited working depth (not using 2P excitation for tracking) but also suffer from loss of signals due to the non-overlapping excitation and collection efficiency peaks in spatial filtering. Currently there is no single solution to all of the above issues.

Molecular trafficking within cells, tissues, and engineered 3D multicellular models is critical to the understanding of the development and treatment of various diseases including cancer. However, current tracking methods are either confined to two dimensions or limited to an interrogation depth of about 15 μm.

A 3D tracking method is presented herein capable of quantifying rapid molecular transport dynamics in highly scattering environments at depths up to 200 μm. The temporal resolution and a spatial localization precision as good as 50 μs and 35 nm have been verified. Built upon spatiotemporally multiplexed two-photon excitation, this approach requires only one detector for 3D particle tracking and allows for two-photon, multicolor imaging. 3D tracking of EGFR complexes at a depth of approximately 100 μm in tumor spheroids is presented herein.

Embodiments disclosed herein, coined TSUNAMI (Tracking Single-particles Using Nonlinear And Multi-plexed Illumination), are capable of tracking particles at depths up to 200 μm in scattering samples with 22/90 [xy/z] nm spatial localization precision and 50 μs temporal resolution. At shallow depths the localization precision can be as good as 35 nm in all three dimensions. The approach is based on passive pulse splitters used for nonlinear microscopy to achieve spatiotemporally multiplexed 2P excitation and temporally demultiplexed detection to discern the 3D position of the particle. The z-tracking range is up to approximately 50 μm (limited by the objective z-piezo stage) and the method enables simultaneous fluorescence lifetime measurements on the tracked particles. A major advantage of this method over previous tracking approaches is that it requires only one detector for SPT and is compatible with multi-color two-photon microscopy.

The technology uses a unique spatiotemporally multi-plexed point-spread function (PSF). Traditional PSFs are circular and comprised of a single excitation beam. This novel PSF uses 4 temporally offset beams (offset in 3.3 ns increments in particular embodiments) that illuminate a tetrahedral pattern in image space. This PSF is achieved by a passive optical system placed before the scanning optics of a traditional two-photon microscope. In certain embodiments, the tracking algorithm utilizes Time-Correlated-Single-Photon Counting (TCSPC) electronics (Becker & Hickl SPC-150) with 19.5 ps time resolution to demultiplex the fluorescent decay from 4 excitation beams and yield the signal that can be processed to achieve sub-diffraction localization of a single particle. To track the particle with the localization signal galvanometric mirrors (xy scanning) and an objective focusing piezo stage (z-dimension) actuate.

SUMMARY

Exemplary embodiments of the present disclosure comprise optical systems and methods (including methods implemented using software) suited for sub-diffraction limited three-dimensional localization of nanometer-scale particles. In exemplary embodiments, the optical systems and methods can be used with conventional two-photon microscopy equipment to perform high speed (up to 50 μs temporal resolution), high precision (up to 35 nm), and deep tissue (up to 200 μm) three-dimensional single-particle tracking. Exemplary embodiments can be configured for single-molecule studies of biological diffusion and transport processes.

Exemplary embodiments include a system comprising: a light source; a plurality of beam splitters configured to separate an input light beam emitted from the light source into a plurality of excitation light beams; a first optical component configured to direct one or more of the excitation light beams in a first lateral dimension; a second optical component configured to direct one or more of the excitation light beams in a second lateral dimension; a third optical component configured to adjust the collimation of one or more of the excitation light beams; and an output beam splitter configured to transmit a first pair of excitation beams and configured to reflect a second pair of excitation beams, where the first pair of excitation beams and the second pair of excitation beams comprise spatiotemporally multiplexed light beams.

In certain embodiments, the first pair of excitation beams transmitted by the output beam splitter comprises a first excitation beam and a second excitation beam, and the first excitation beam is temporally offset between 1 and 20 nanoseconds from the second excitation beam. In particular embodiments, the second pair of excitation beams transmitted by the output beam splitter comprises a third excitation beam and a fourth excitation beam, and the third excitation beam is temporally offset between 1 and 20 nanoseconds from the fourth excitation beam. In some embodiments, the third excitation beam is temporally offset between 1 and 20 nanoseconds from the second excitation beam. In particular embodiments, the first pair of excitation beams transmitted by the output beam splitter comprises a first excitation beam and a second excitation beam, and the first excitation beam is temporally offset between 1 and 10 nanoseconds from the second excitation beam.

In specific embodiments, the second pair of excitation beams transmitted by the output beam splitter comprises a third excitation beam and a fourth excitation beam, and the third excitation beam is temporally offset between 1 and 10 nanoseconds from the fourth excitation beam.

In certain embodiments, the third excitation beam is temporally offset between 1 and 10 nanoseconds from the second excitation beam. In particular embodiments, the first pair of excitation beams and the second pair of excitation beams illuminate a polyhedral pattern in an image space. Some embodiments comprise a two-photon microscope and a plurality of optical detectors, where the first pair of excitation beams and the second pair of excitation beams are directed to the two-photon microscope. In certain embodiments, the plurality of optical detectors are configured as single-photon counting modules. In particular embodiments, the optical detectors are coupled to a processor comprising an algorithm configured to process a plurality of signals produced by the optical detectors.

In some embodiments, the algorithm is configured to demultiplex a fluorescent decay from a single particle illuminated by the first, second, third, and fourth excitation beams, and wherein the algorithm is configured to provide an output signal that can be processed to achieve sub-diffraction localization of the single particle. In specific embodiments, the output beam splitter is a polarizing beam splitter. In certain embodiments, the plurality of beam splitters comprises s-polarized and p-polarized low group velocity dispersion beam splitters. In particular embodiments, the first optical component and the second optical component are galvanic mirrors and the third optical component is a lens. In some embodiments, the light source is a laser configured to emit light at a wavelength between 800-900 nm and a pulse width of 50-1000 femtoseconds.

Exemplary embodiments include a method of tracking a single particle, where the method comprises: separating an input light beam emitted from a light source into a plurality of excitation light beams that are spatially and temporally offset; illuminating a single particle with the plurality of light beams that are spatially and temporally offset' detecting fluorescence emitted from the single particle; and processing photon histogram data resulting from the illumination of the single particle by the plurality of excitation light beams that are spatially and temporally offset to determine a location of the single particle at specific time.

In certain embodiments, processing photon histogram data comprises: counting and correlating signal photons to a reference clock; extracting count values from a photon histogram; selecting a plurality of windows from the photon histogram; obtaining a time gate value from an average value for each window of the photon histogram; applying a fluorescence correction factor to the time gate value to generate a corrected time gate value for each window of the photon histogram; subtracting dark count values from the corrected time gate value for each window of the photon histogram; calculating error signals from normalized time window differences; applying proportional control gain values to the error signals; and performing geometric transform to switch from point-spread function error vectors to galvanic space error vectors.

In particular embodiments, the input light beam emitted from the light source is separated into the plurality of excitation light beams via passive beam splitters. In some embodiments, the plurality of excitation light beams that are spatially and temporally offset comprises a first light beam and a second light beam; and the first light beam is temporally offset between 1 and 20 nanoseconds from the second light beam. In specific embodiments, the plurality of excitation light beams that are spatially and temporally offset comprises a third light beam and a fourth light beam; and the third light beam is temporally offset between 1 and 20 nanoseconds from the fourth light beam. In certain embodiments, the third excitation beam is temporally offset between 1 and 20 nanoseconds from the second excitation beam.

In particular embodiments, the plurality of excitation light beams that are spatially and temporally offset comprises a first light beam and a second light beam; and the first light beam is temporally offset between 1 and 10 nanoseconds from the second light beam. In some embodiments, the plurality of excitation light beams that are spatially and temporally offset comprises a third light beam and a fourth light beam; and the third light beam is temporally offset between 1 and 10 nanoseconds from the fourth light beam. In specific embodiments, the third beam is temporally offset between 1 and 10 nanoseconds from the second beam. In certain embodiments, the plurality of excitation light beams that are spatially and temporally offset illuminate a tetrahedral pattern in an image space. In particular embodiments, the fluorescence emitted from the single particle is excited by a pulsed laser. In some embodiments, the fluorescence emitted from the single particle is detected by a two-photon microscope. In specific embodiments, the two-photon microscope is coupled to a plurality of optical detectors. In certain embodiments, the plurality of optical detectors are configured as photomultipler tubes. In certain embodiments, the optical detectors are coupled to a processor comprising an algorithm configured to process photon histogram data resulting from the illumination of the single particle by the plurality of excitation light beams that are spatially and temporally offset to determine a location of the single particle at specific time.

In particular embodiments, processing photon histogram data comprises: generating an output signal by demultiplexing a fluorescent decay from the single particle illuminated by the plurality of light beams that are spatially and temporally offset; and processing the output signal to achieve sub-diffraction localization of the single particle. In some embodiments, the plurality of excitation light beams that are spatially and temporally offset are directed to a plurality of passive beam splitters. In specific embodiments, the plurality of passive beam splitters comprises s-polarized and p-polarized low group velocity dispersion beam splitters. In certain embodiments, the plurality of excitation light beams that are spatially and temporally offset are directed to a plurality of galvanic mirrors. In particular embodiments, the plurality of excitation light beams that are spatially and temporally offset are directed to a collimation lens. In specific embodiments, the input light beam is generated by a laser configured to emit light at a wavelength between 800-900 nm and a pulse width of 100-200 femtoseconds.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Exemplary embodiments of the present disclosure utilize a unique spatiotemporally multiplexed point-spread function (PSF). Traditional PSFs are circular and comprised of a single excitation beam. Particular embodiments of the novel PSF disclosed herein utilizes four temporally offset beams (e.g. with offset increments measured in the nanosecond range) that illuminate a tetrahedral pattern in image space. The PSF can be achieved by a passive optical system placed before the scanning optics of a traditional two-photon microscope.

In specific embodiments, the tracking algorithm can utilize Time-Correlated-Single-Photon Counting (TCSPC) electronics (e.g. Becker & Hickl SPC-150) with picosecond time resolution (e.g. 19.5 ps resolution in one particular embodiment) to demultiplex the fluorescent decay from four excitation beams and yield the signal that can be processed to achieve sub-diffraction localization of a single particle. In order to track the particle with the localization signal, galvanometric mirrors (x-y scanning) and an objective focusing piezo stage (z-dimension) can actuate the focal plane in sample space to keep up with the freely diffusing particle.

Figure 1:
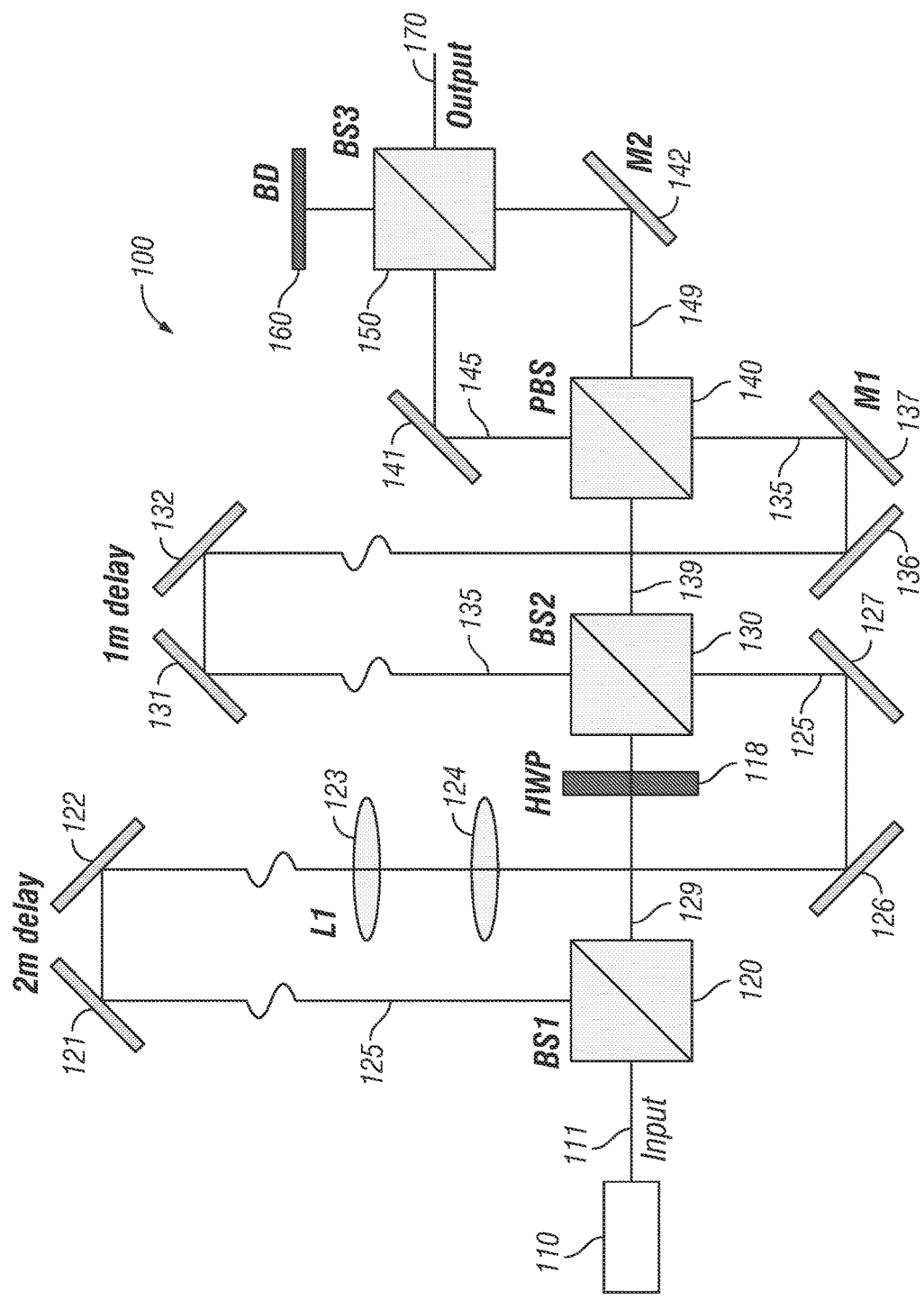
FIG. 1 illustrates a schematic view of a beam multiplexer according to exemplary embodiments of the present disclosure.

Referring now to the exemplary embodiment shown in FIG. 1, a beam multiplexer system 100 comprises a light source 110 emitting light 111 to a beam splitter 120 which reflects a portion of light 125 emitted from light source 110 to a pair of mirrors 121, 122. Light 125 is directed from mirrors 121, 122 through lenses 123, 124 and then to mirrors 126, 127. A portion of light 129 is transmitted through beam splitter 120 and passes through half wave plate 118 before entering beam splitter 130. Beam splitter 130 reflects a portion of light 129 and transmits a portion of light 125 to a first pair of mirrors 131, 132 and a second pair of mirrors 136, 137. This light is shown as a light beam 135 comprising the reflected portion of light 129 and the transmitted portion of light 125 (which has been delayed with respect to light 129).

In addition, beam splitter 130 transmits a portion of light 129 and reflects a portion of light 125 as a light beam 139 to a polarized beam splitter 140. Polarized beam splitter 140 reflects a portion of light beam 139 and transmits a portion light beam 135 (which has been further delayed with respect to light 139) as a light beam 145. In addition, polarized beam splitter 140 transmits a portion of light beam 139 and reflects a portion of light beam 135 as a light beam 149.

Beam splitter 150 reflects a portion of light beam 145 to a beam dump 160 and transmits a portion of light beam 149 to beam dump 160. Beam splitter 150 also transmits a portion of light beam 145 and reflects a portion of light beam 149 as an output beam 170 in a spatiotemporally multiplexed point-spread function (PSF). In the embodiment shown, output beam 170 includes four temporally and spatially offset beams that can be used to illuminate a tetrahedral pattern in image space.

In order to spatially separate the light beams in image space, mirrors 137 and 142 and lens 123 can be adjusted. In certain embodiments, mirror 137 can control separation of beam 135 into a beam pair in the x-dimension, while mirror 142 can control beam separation of beam 149 in the y-dimension. In certain embodiments, lens 123 is part of a telescope assembly that can adjust collimation of beam 125 (which is a component of beam 135) thus changing its focal plane (z-offset) relative to beam 129 (which is a component of beam 139). To recombine beams 135 and 139 and create the desired pair offsets, polarizing beam splitter 140 can be used, followed by beam splitter 150, which can be configured as a standard 50:50 beamsplitter. The placement of the four beam splitters 120, 130, 140 and 150 relative to the adjustment optics creates a PSF that can be used for sub-diffraction localization of particles.

In particular embodiments, light source 110 is configured as a Ti:Al$_2$O$_3$ laser with 800-900 nm wavelength, 76 MHz repetition, and 150 µs pulse width. In certain embodiments, beam splitters 120 and 130 are 50:50 beam splitters and the light pulses are delayed in time by 3.3 ns each using two physical delay lines. In specific embodiments, the delay line incorporating mirrors 121, 122 is approximately two meters in length and the delay line incorporating mirrors 131, 132 is approximately one meter in length.

Figure 2:
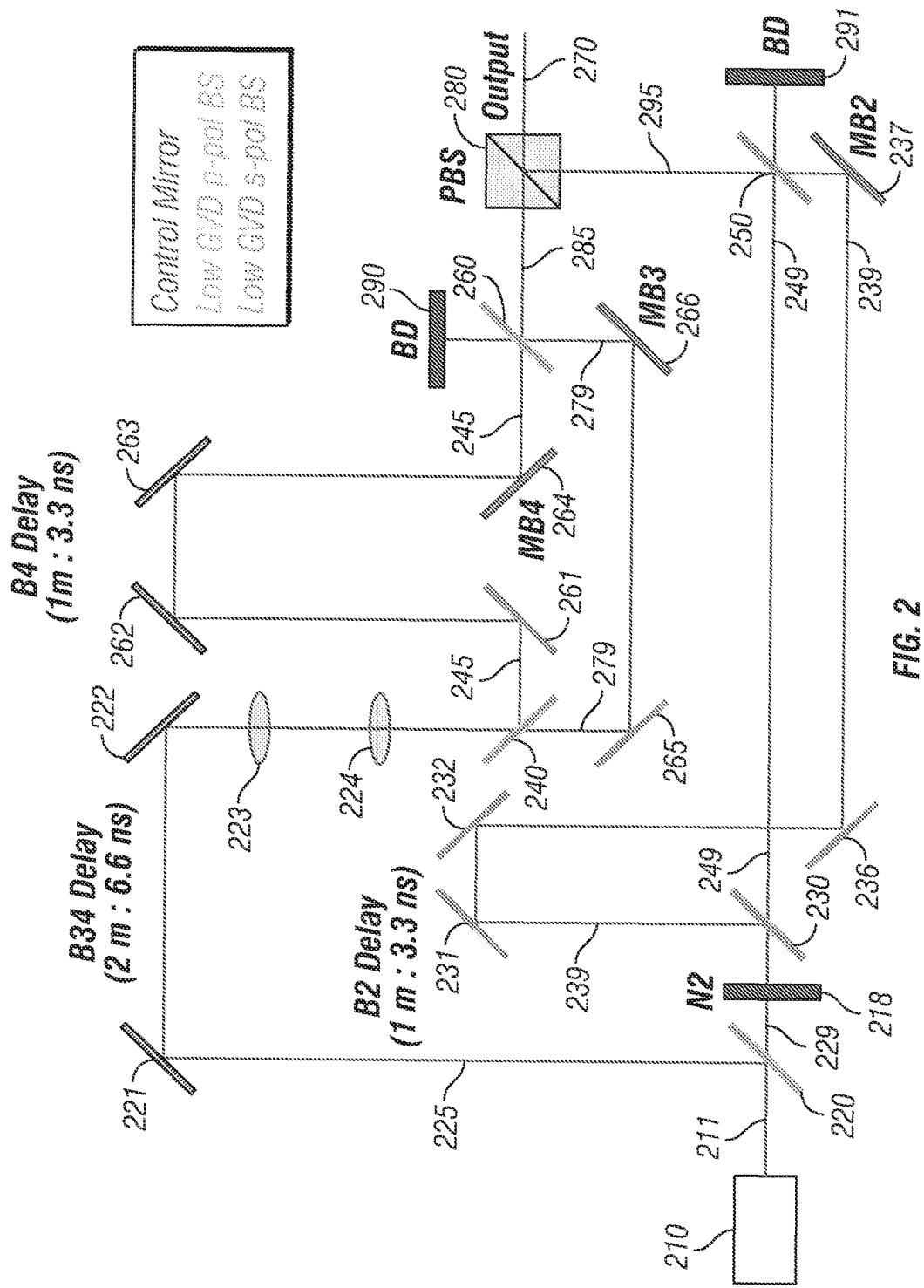
FIG. 2 illustrates a schematic view of a beam multiplexer according to exemplary embodiments of the present disclosure.

Other embodiments of the present disclosure may comprise a different configuration of components. For example, referring to the embodiment shown in FIG. 2, a beam multiplexer system 200 comprises a light source 210 emitting light 211 to a beam splitter 220 which reflects a portion of light 225 emitted from light source 210 to a pair of mirrors 221, 222. In this embodiment, beam splitter 220 is configured as a low group velocity dispersion (GVD) p-polarized beam splitter. Light 225 is directed from mirrors 221, 222 through lenses 223, 224 and then to beam splitter 240, which is also configured as a low GVD p-polarized beam splitter.

A portion of light 229 is transmitted through beam splitter 220 and passes through half wave plate 218 before entering beam splitter 230 which is configured as a low GVD s-polarized beam splitter in this embodiment. Beam splitter 230 reflects a portion of light 239 to a first pair of mirrors 231, 232 and a second pair of mirrors 236, 237. In addition, beam splitter 230 transmits a portion of light 249 to a beam splitter 250 that is also configured as a low GVD s-polarized beam splitter in this embodiment.

Beam splitter 250 reflects a portion of light 239 to a beam dump 295 and transmits a portion of light 249 to beam dump 291. In addition, beam splitter 250 transmits a portion of light 239 and reflects a portion light 249 as a light beam 295 to a polarized beam splitter 280. In the embodiment shown, light 239 is temporally delayed with respect to light 249.

Referring back now to light beam 225, beam splitter 240 reflects a portion of light 245 and transmits a portion of light 279. Light 245 is directed by mirrors 261, 262, 263 and 264 to a beam splitter 260, which is configured as a low GVD p-polarized beam splitter in this embodiment. Light 279 is directed by mirrors 265 and 266 to beam splitter 260. In the embodiment shown, light 245 is temporally delayed with respect to light 279.

Beam splitter 260 reflects a portion of light 245 to a beam dump 290 and transmits a portion of light 279 to beam dump 160. In addition, beam splitter 260 transmits a portion of light 245 and reflects a portion light 279 as a light beam 285 to polarized beam splitter 280.

Polarized beam splitter 280 reflects a portion of light beam 295 and transmits a portion of dual light beam 285 to create output beam 270. In the embodiment shown, mirrors 237, 264 and 266 can be used to position the light beams in the X-Y plane (similar to mirrors 137 and 142 in the previous embodiment). In addition, lens 223 can be adjusted to adjust collimation of the light beams (similar to lens 123 in the previously described embodiment).

Control Schematic

Figure 3:
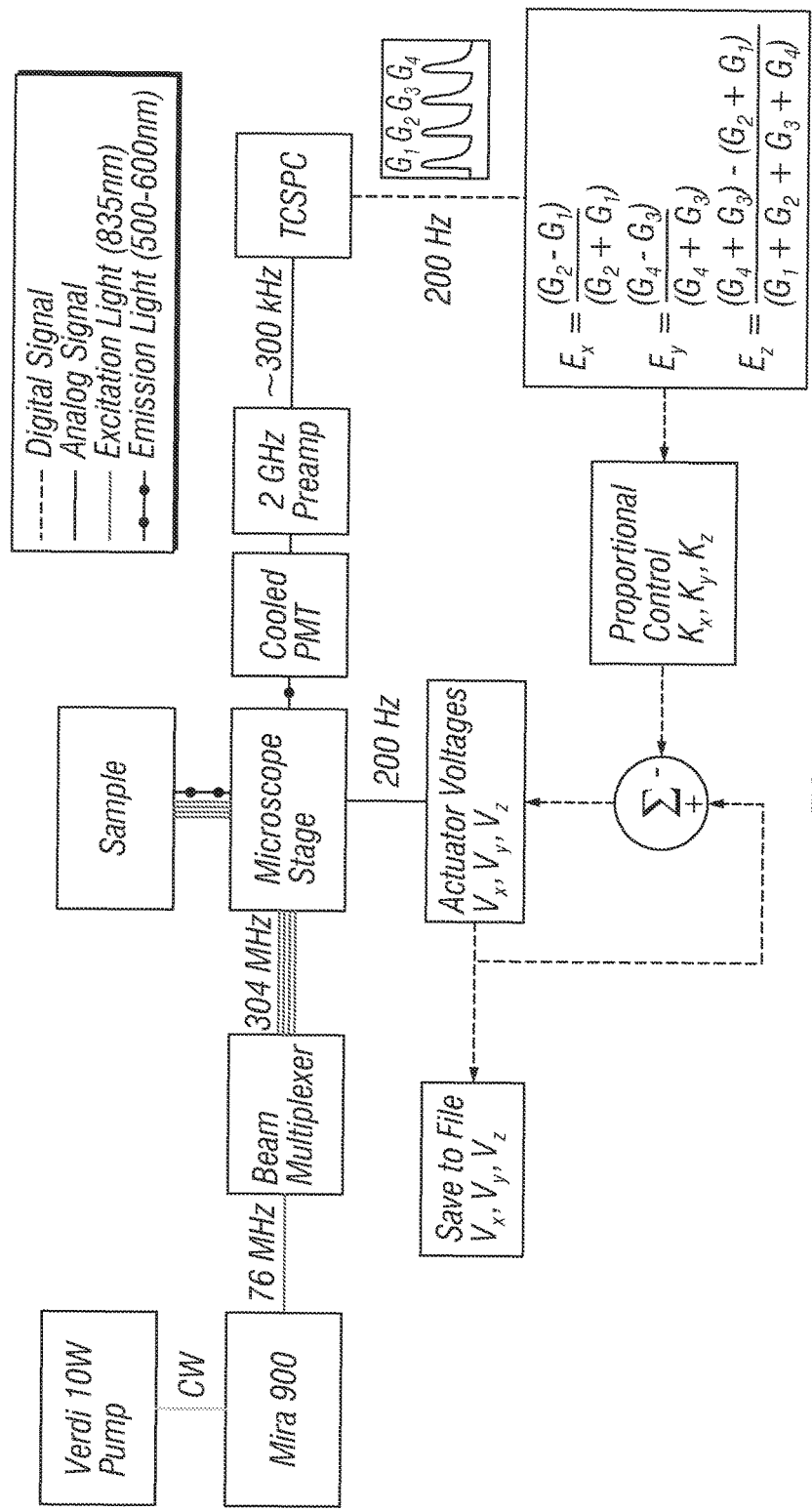
FIG. 3 illustrates a control schematic according to exemplary embodiments of the present disclosure.

Referring now to FIG. 3, one exemplary embodiment of a control schematic for the systems disclosed herein shows system level interaction and feedback control loop. In this embodiment, a free running 76 MHz pulse train generated by a Ti:Al2O3 oscillator (Mira 900, Coherent) passes through the beam multiplexer and onto the sample. Fluorescence is detected by a cooled low dark count PMT (H7422P-40, Hamamatsu Corp.) and amplified with a 2 GHz cutoff bandwidth preamplifier (HFAC-26, Becker and Hickl GmbH). The amplified analog signal is then counted and correlated to the reference clock of the Ti:Al2O3 oscillator with a PCI-based photon counting board (SPC-150, Becker and Hickl GmbH). In this embodiment, every 1-5 ms a photon histogram is polled from the TSCPC module and processed in the software loop run in LabVIEW (National Instruments). The tracking algorithm employs a proportional control to convert the error signals to new stage positions. New voltages are sent out through a DAQ (PCIe-6353, National Instruments) to their respective actuators, scan mirrors for X and Y, piezo objective stage for Z.

Due to the time dependent nature of this measurement technique it is important that the control loop operates at the desired frequency, typically 5 ms. To achieve this deterministic requirement in windows operating system the LabVIEW control loop can be driven by an external hardware timed clock (counter from PCIe-6353 board). Using this method, deterministic loops can be achieved with rates up to 2 kHz without missing a hardware clock tick. For a typical 8 minute trajectory there are no missed loops out of 96,000 requested with a 5 ms (200 Hz) control loop period.

Figure 4:
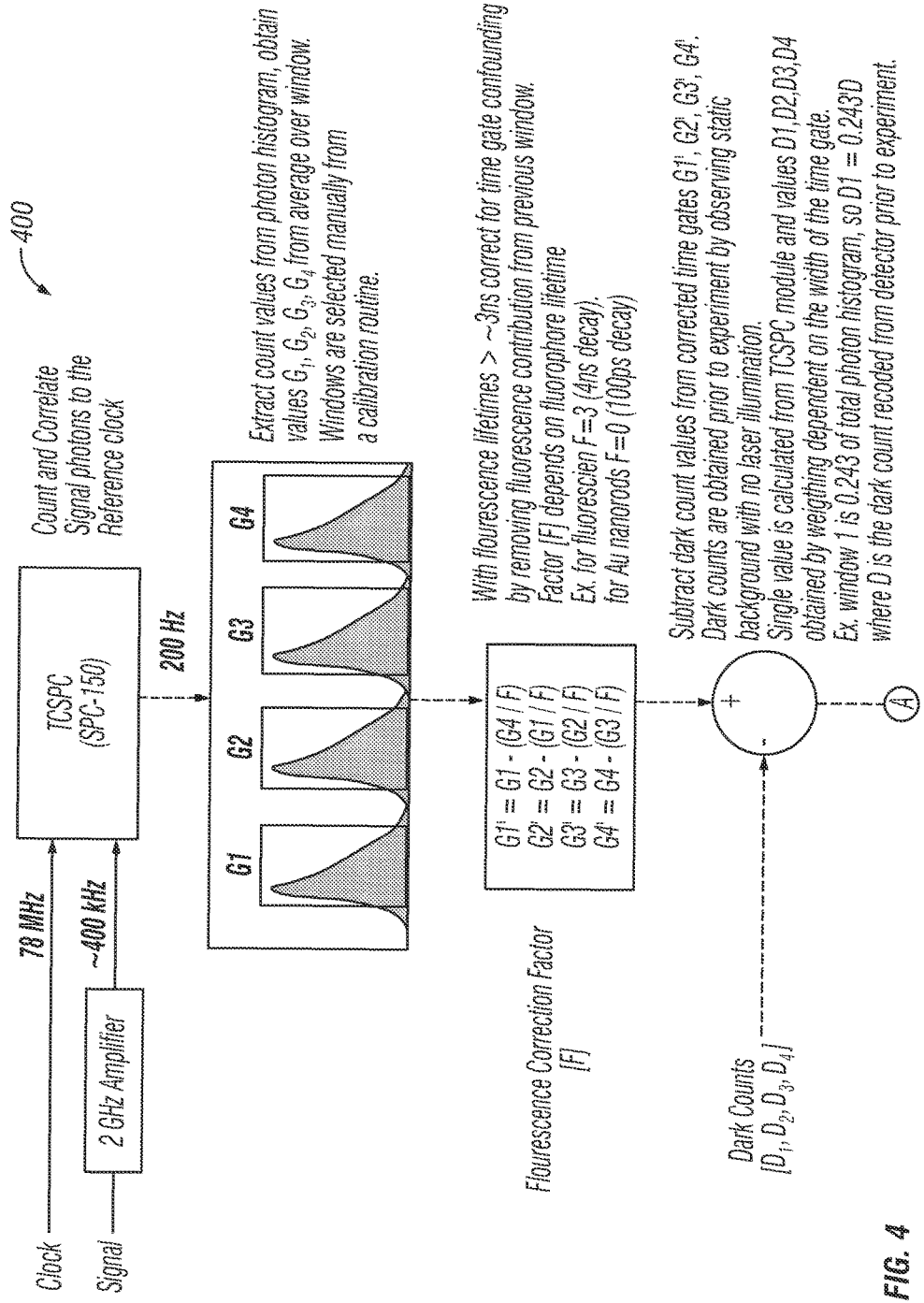
FIG. 4 illustrates an algorithm flowchart according to exemplary embodiments of the present disclosure.
Figure 4:
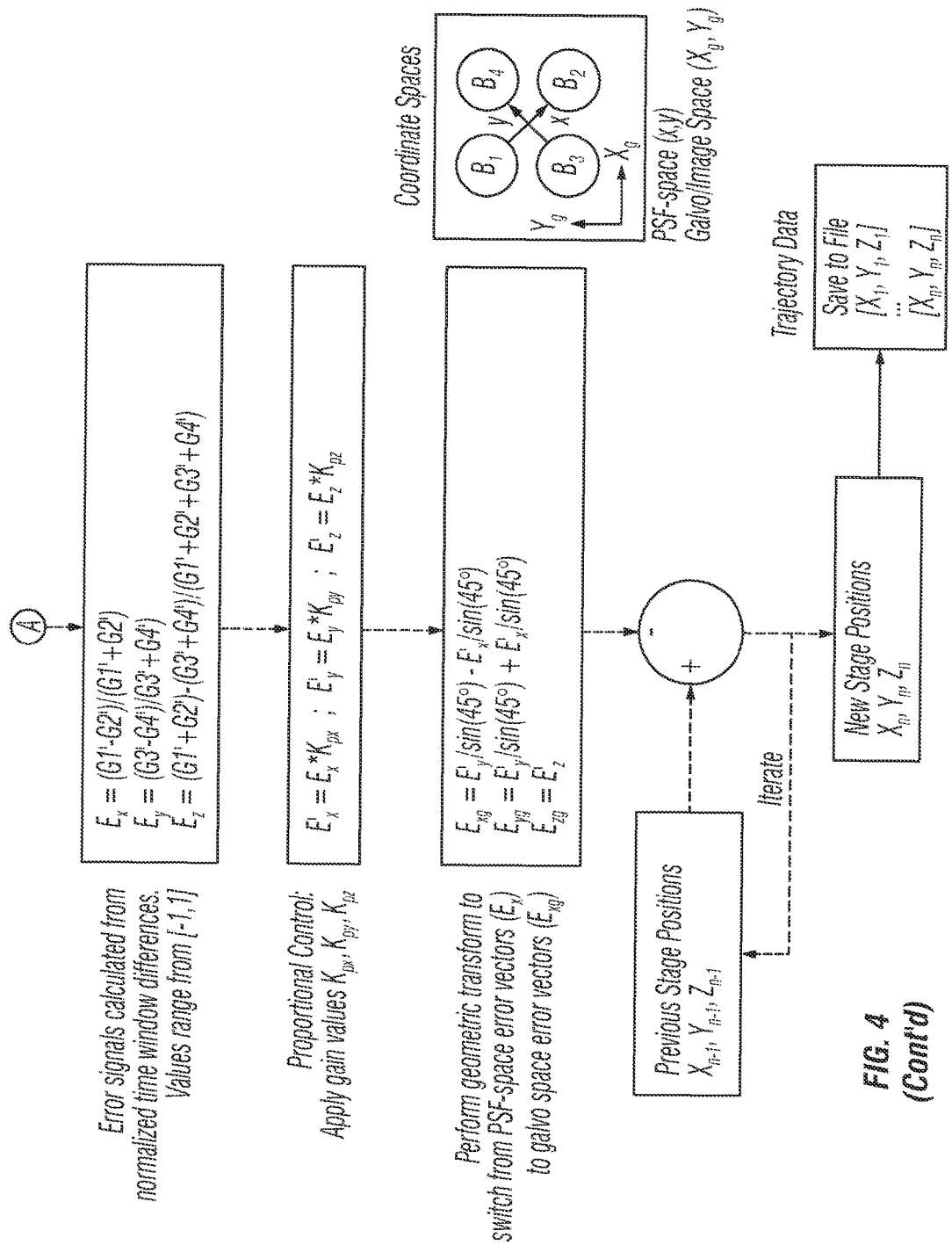

Referring now to FIG. 4, an algorithm flowchart 400 for the systems disclosed herein depicts the steps used by the software during operation. In the first step, the algorithm counts and correlates the signal photons to the reference clock. Then, the algorithm extracts count values from the photon histogram, and obtains values G1, G2, G3 and G4 from the average over the window. The windows can be selected manually from a calibration routine. A fluorescence correction factor [F] is calculated. With fluorescence greater than about 3 ns, time gate confounding is corrected by removing fluorescence contribution from the previous window. Factor [F] depends on fluorophore lifetime. For example, for fluorescein F=3 (4 ns decay) and ford Au nanorods F=0 (100 ps decay).

The algorithm then subtracts dark count values from corrected time gates G1', G2', G3' and G4'. Dark counts are obtained prior to experiment by observing static background with no laser illumination. A single value is calculated from the TCSPC module and values D1, D2, D3 and D4 are obtained by weighting dependent on the width of the time gate.

For example, window 1 is 0.243 of the total photon histogram, so D1=0.243*D where D is the dark count recoded from the detector prior to the experiment.

Error signals can then be calculated from normalized time window differences. Values range from [−1, 1]. The algorithm then applies gain values Kpx, Kpy and Kpz. The algorithm also performs a geometric transform to switch from PSF-space error vectors (Ex) to galvo space error vectors (Exg). Additional details and functions of the algorithm are shown in FIG. 4.

Experimental Results

Exemplary embodiments of the present disclosure are capable of tracking particles at depths up to 200 μm in scattering samples with 22/90 [xy/z] nm spatial localization precision and 50 μs temporal resolution. At shallow depths the localization precision can be as good as 35 nm in all three dimensions. The approach is based on passive pulse splitters used for nonlinear microscopy [24] to achieve spatiotemporally multiplexed 2P excitation and temporally demultiplexed detection [25] to discern the three-dimensional position of the particle. In one embodiment, the z-tracking range is up to approximately ±50 μm (limited by the objective z-piezo stage) and the method enables simultaneous fluorescence lifetime measurements on the tracked particles. One advantage of this method over previous tracking approaches is that it requires only one detector for SPT and is compatible with multi-color two-photon microscopy. Capabilities of exemplary embodiments are demonstrated by tracking single fluorescent beads in aqueous solutions that include scattering, as well as tracking prescribed motions in these controlled environments.

Exemplary embodiments can also demonstrate tracking of EGFR (epidermal growth factor receptor) complexes tagged with fluorescent beads in tumor spheroids, demonstrating deep 3D SPT in multicellular models. This technique may be referred to herein as TSUNAMI (Tracking Single-particles Using Nonlinear And Multiplexed Illumination).

Spatiotemporal Multiplexer Design

In the spatiotemporal multiplexed scheme, laser pulses emitted with a 13 ns period from a Ti:sapphire oscillator are separated into four beams, which are delayed by 3.3 ns each and focused through a high-N.A. objective at slightly offset xyz positions. The four resulting 2P-excitation volumes are arranged into a barely overlapped, tetrahedral geometry (see FIG. 5c), to generate selective excitation equivalent to the spatial filtering condition in the previous four-detector confocal tracking setup (15) with each 2P-excitation volume receiving laser pulses at a different time delay. For a fluorescent particle residing somewhere inside the excitation tetrahedron, its 2P emission is collected by a photomultiplier tube (PMT1 in FIG. 5a). Through time-correlated-single-photon counting (TCSPC) detection, each detected photon is assigned to a specific time gate (G1-G4, here assuming the decay time is approximately 4 ns or less) in the fluorescence decay histogram (FIG. 5b), and therefore attributed to an individual excitation volume. For a particle sitting at the center of the tetrahedron, the resulting photon counts are approximately equal in all four time gates. An offset of the particle from the tetrahedron center can be estimated from the normalized photon count differences in the four time gates (i.e. error signals Ex, Ey and Ez in FIG. 3). Once the particle position offset is determined, a closed feedback loop then steers galvanometer mirrors and the objective z-piezo stage to lock the tracking beams on the particle. A particle's 3D trajectory is therefore determined directly from the controller output sent to the galvanometer and piezo actuators.

Figure 5A:
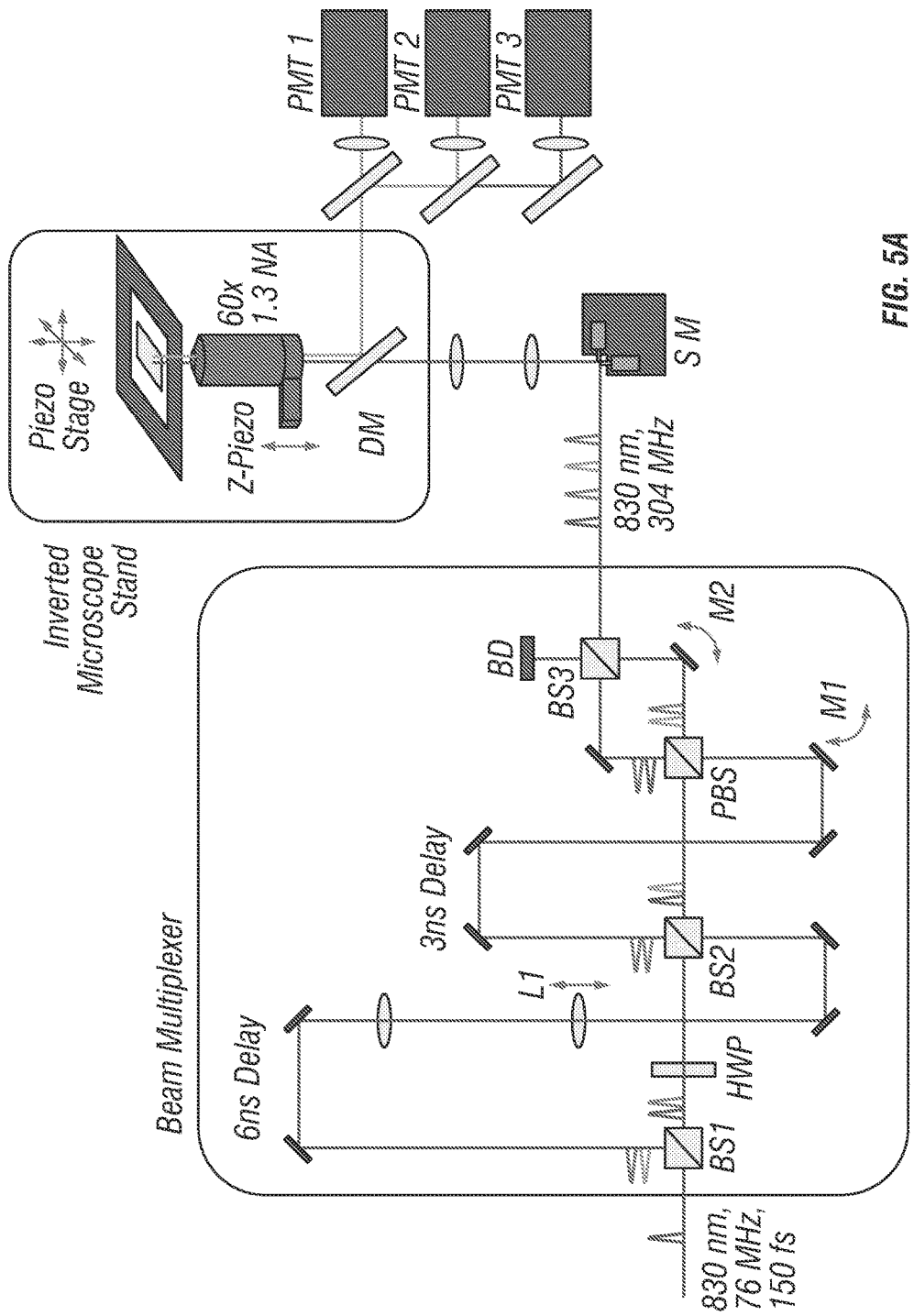
FIG. 5 illustrates a schematic view of a system and data obtained from the system according to exemplary embodiments of the present disclosure.
Figure 7A:
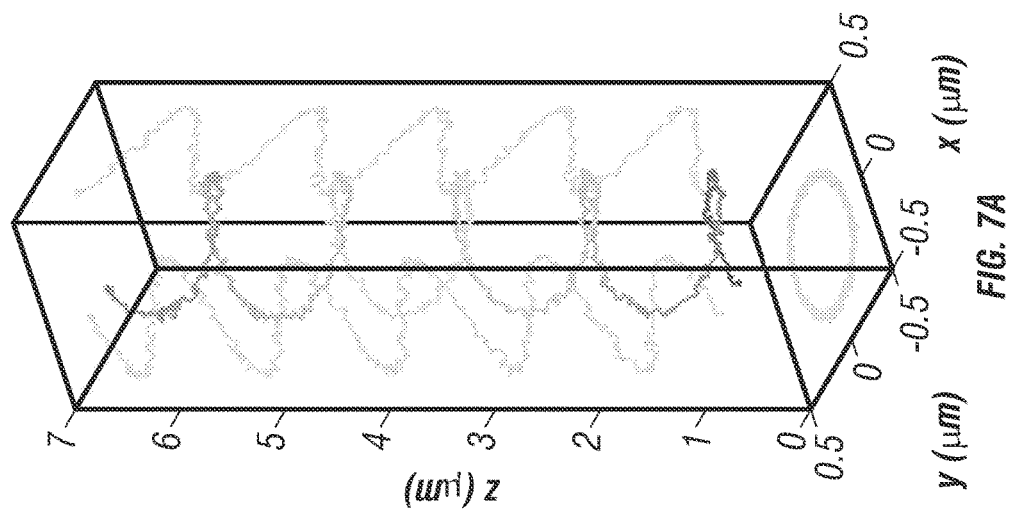
FIG. 7 shows data relating to characterization of directed motion and free diffusion.

FIG. 5a shows a schematic of an embodiment with a two-photon 3D tracking microscope. Spatiotemporal multiplexing is enabled through the beam multiplexer optical system which utilizes 2 beam-splitters (BS1 and BS2) configured in a recombination design to generate 4 beams which can be quasi-independently controlled via mirrors (M1 and M2). Physical delay lines can be tuned to provide temporal separation. In this case 6.6 ns (2 meters) and 3.3 ns (1 meter) path length delay lines create 4 beams with a period of 3.3 ns corresponding to an even division of the fundamental 13 ns period generated by the laser oscillator used (Mira 900, Coherent). Tracking actuation is performed using scanning mirrors (SM) and an objective focusing stage (Z-Piezo).

FIG. 5b show photon counting histogram of a particle centered in the middle of the four-excitation focus demonstrating temporal offsets and power balance between the independent excitation beams. FIG. 5c shows an idealized image space projection of the tetrahedral PSF. Beam spacing has been exaggerated to demonstrate offsets, tuning can easily be performed by manual alignment continuously over a range of 100 nm to tens of micrometers. d. Experimental laser scanning image of a single 100 nm diameter fluorescent bead with simultaneous 4 beam excitation. Scale bar is 1 μm. HWP is half-wave plate, PBS is polarizing beamsplitter, DM is dichroic mirror, and BD is beam dump.

Spatiotemporal multiplexing has previously been explored for diffusion measurements [26] and tracking [27] but these methods rely on a picosecond pulsed laser for one photon excitation and therefore are not suitable for use in multicellular models or tissues. Furthermore, only one photomultiplier tube (PMT1 in FIG. 5a) is needed for SPT in exemplary embodiments of the present disclosure, whereas 3 to 5 detectors are needed in confocal tracking setups (14-16). In addition the fluorescence lifetime of the tracked particle is readily determined from the time-resolved photon data (see FIG. 6) [21]. As the laser beam is steered by active feedback to lock on the tracked particle, a large tracking range is achieved (approximately ±50 μm in z direction and approximately 100 μm in x-y) with minimal perturbation to the samples (whereas some confocal setups require the sample to be moved in order for SPT [14,15].

Calibration and Localization Precision Characterization

To validate the TSUNAMI microscope, fluorescent beads were first tracked (diameter 100 nm, decay time about 3.9 ns) in aqueous solution (see FIG. 7) and in 9% gelatin gel with 1% intralipid (a highly scattering environment; see FIG. 8). By following prescribed motions in these controlled environments [2] the localization precision, tracking speed limits, temporal resolution, and tracking depth of the system were successfully characterized.

From optical modeling, the optimal lateral and vertical separation distances between the two-photon excitation volumes were estimated to be 500 nm and 1,000 nm, respectively (see FIG. 9) [23]. The alignment of the four excitation beams was verified by volumetric scanning of a fixed fluorescent bead (see FIG. 5d). To determine particle localization uncertainty and maximum speed that the system can follow, the inventors tracked a fixed fluorescent bead (diameter 100 nm, F-8803, Life Technologies) loaded on an independent xyz piezo stage (P-733K130, PI) [2]. The independent stage was programmed to move in a helical pattern (see FIG. 7a). At an average speed of 2 μm/s, the estimated tracking errors (r.m.s.) were 16.2 nm in x, 16.7 nm in y, and 35.1 nm in z (see FIG. 10).

FIG. 7 shows characterization of directed motion and free diffusion. FIG. 7a shows an example helical trajectory of a 100 nm diameter fluorescent bead moved through a known path using an independent 3D piezo stage (P-733K130, PI). The path duration was 7 seconds with an average velocity of 2.1 μm/s. The tracking system reproduced the true trajectory accurately with 16.5 nm uncertainty in x and y and 33.3 nm in z. Rainbow coloration corresponds to time with blue representing the beginning of the trajectory. FIG. 7b shows several helical trajectories were performed with varying mean velocities. The particle localization uncertainty increases with increasing velocities up to 10 μm/s, where the particle speed is too fast for the controller to target lock. Within a range of 8 μm/s or less the localization uncertainty is essentially constant, 16 nm for x and y, and 45 nm for z. c. Box plot with histograms of measured versus theoretical diffusion coefficients for 80% wt. glycerol, 50% wt. glycerol, 20% wt. glycerol, and 100% water, respectively. The measured central tendency of the diffusion coefficients were found to agree with the Stokes-Einstein equation for wide range of values (0.07-4.3 μm2/s). The agreement with theory can been seen by how closely the data follow the 1:1 guide line (plotted on semilog scale) d. An example trajectory of a 100 nm diameter fluorescence bead in an 80% wt. glycerol solution, free diffusion was observed over 43 seconds. FIG. 7e. shows particle photon count rate versus time, a monotonically decreasing count rate indicates that a single particle is being tracked. Due to a photobleaching effect the rate decays over the course of the trajectory.

FIG. 10 shows localization uncertainty measurements. FIG. 10a shows additional helical trajectory of ϕ100 nm fluorescent bead (F-8803, Life Technologies) fixed to coverslip and scanned using 3D piezo stage. The scan was programmed for ±800 nm xy range and 6 μm/s mean velocity. FIG. 10b shows additional helical trajectory of ±3 μm xy range and 9.6 μm/s mean velocity. FIG. 10c shows particle brightness over time for trajectory in FIG. 10a, measured in photon counts per second. At high velocities the count rate oscillates due to a slight misbalance in the excitation efficiencies of each beam, this effect was only noticed for helical trajectories with mean velocities higher than 6 μm/s. Localization accuracy remains acceptable even for very high mean velocities up to approximately 10 μm/s where the particle displacement within a 5 ms time-step is too large for the proportional controller to remain locked into the target. FIGS. 10d, 10e, and 10f show localization error graphs for trajectory in FIG. 10a along x, y, and z dimensions respectively. The error value at each time-point was calculated by the difference between the tracking actuator outputs (scan mirrors for xy, objective piezo for z) and the feedback sensor measurements in the 3d path scanning stage. With a sub-nanometer resolution it is assumed that the 3d stage feedback sensors represent the actual position of the stage in a given time point. The localization uncertainty was calculated from the raw error values by taking the root mean squared deviations (rms). The rms deviations of the error signal were 16 nm for x y and 35 nm for z even for high velocities up to 6 μm/s.

Figure 7B:
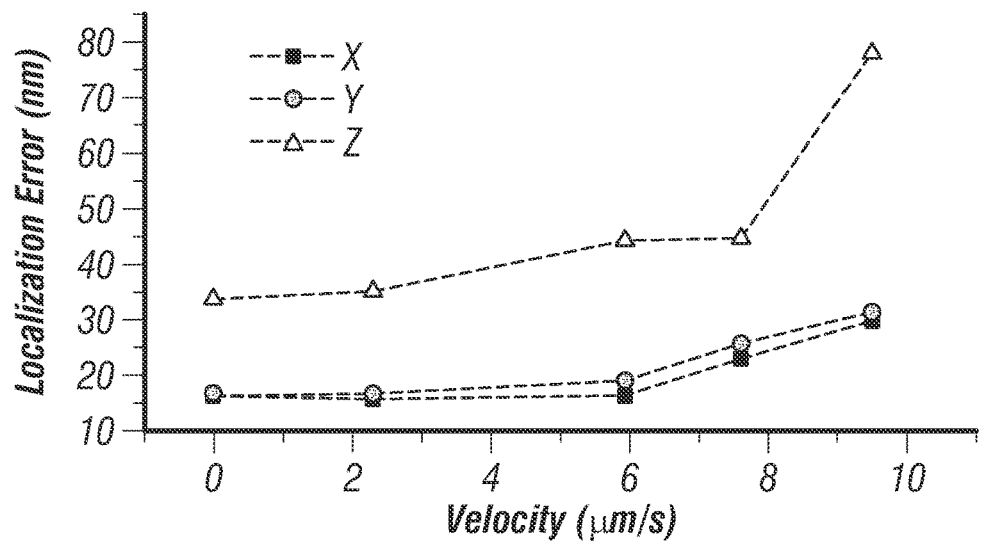
Figure 7C:
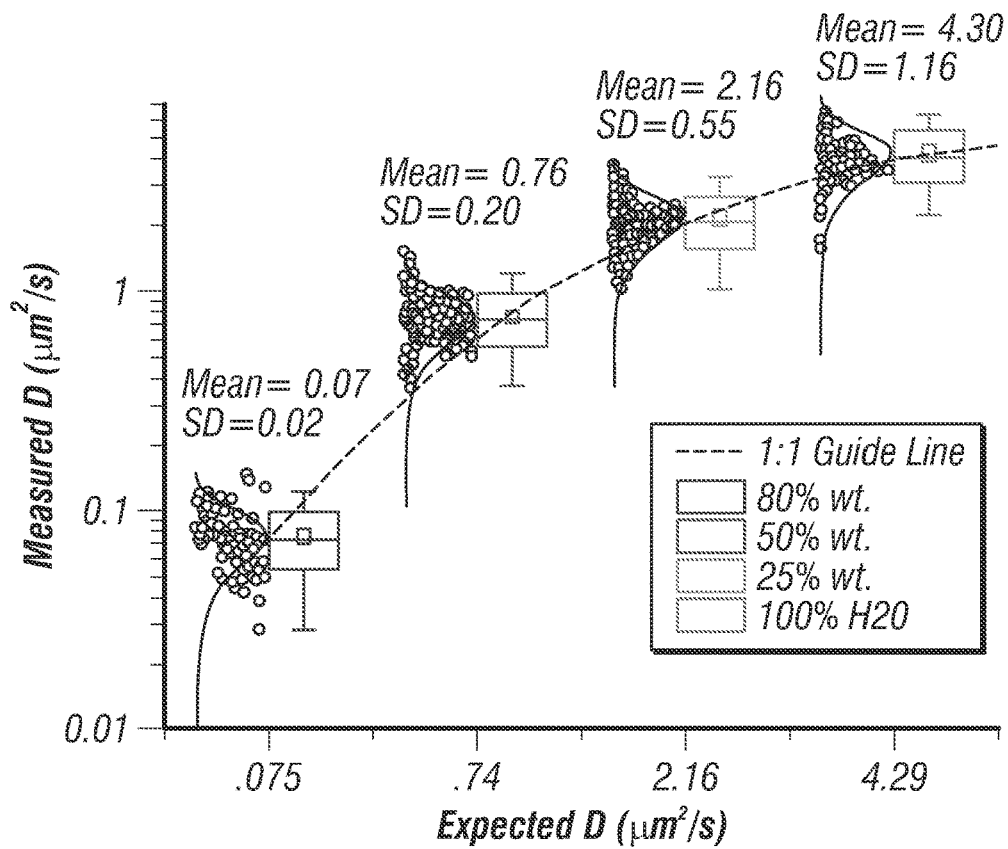
Figure 7D:
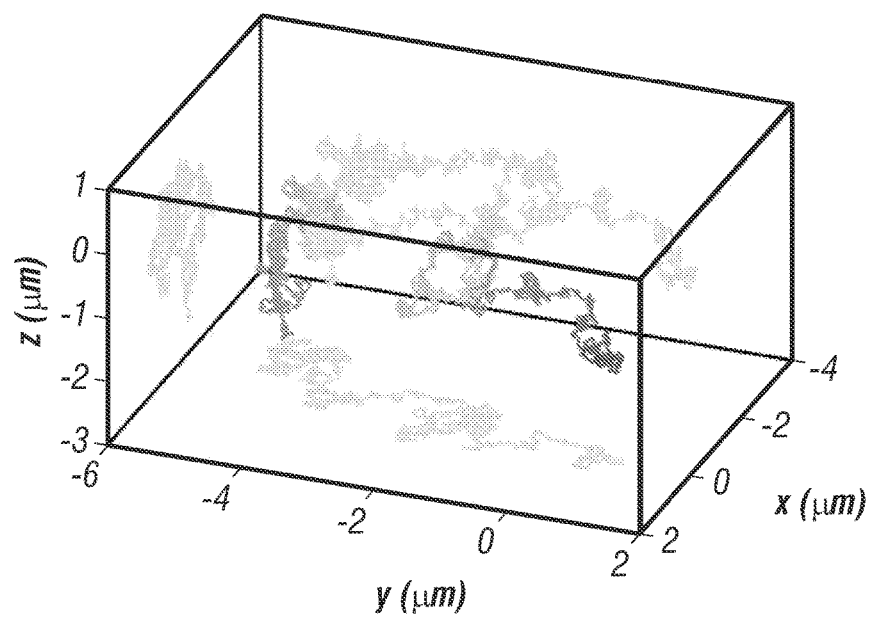
Figure 7E:
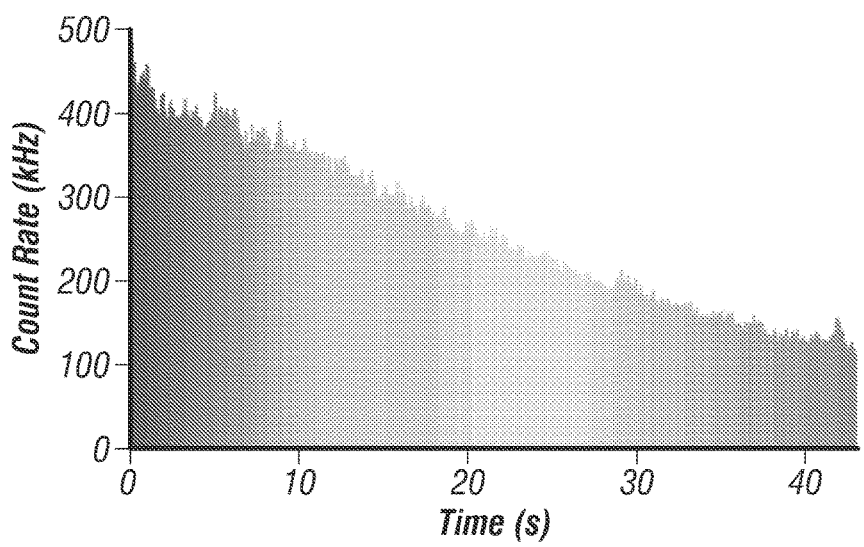
Figures 8A, 8B:
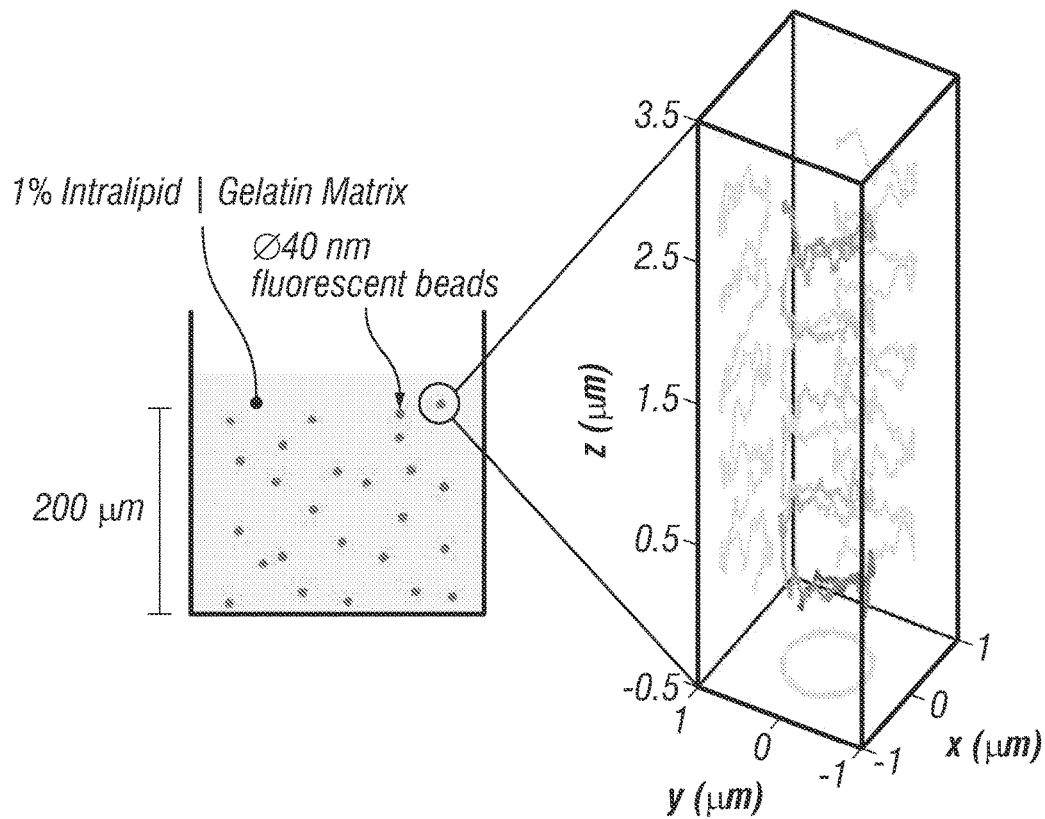
FIG. 8 shows data relating to localization uncertainty through turbid media.
Figure 8C:
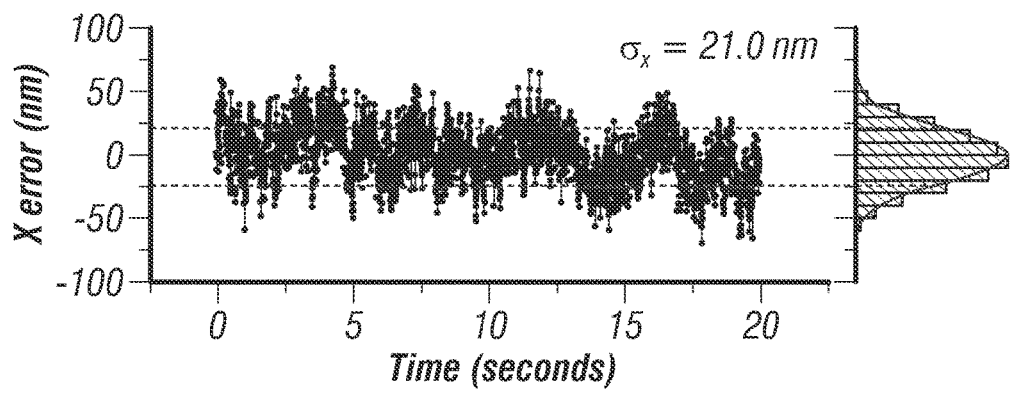
Figure 8D:
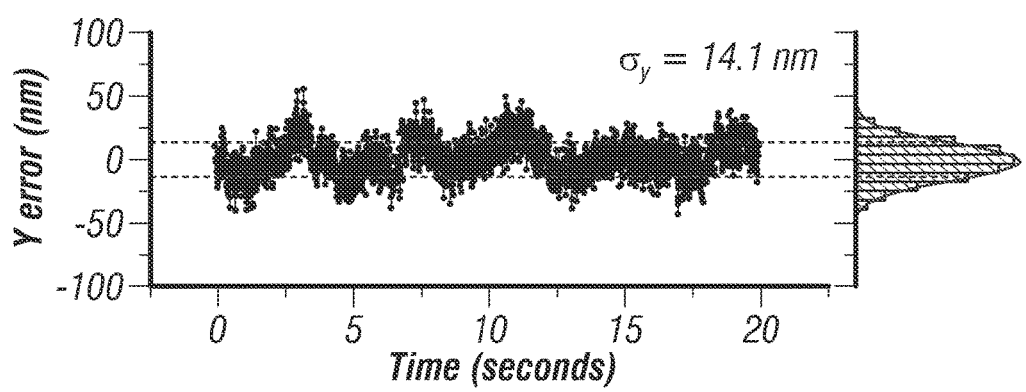
Figure 8E:
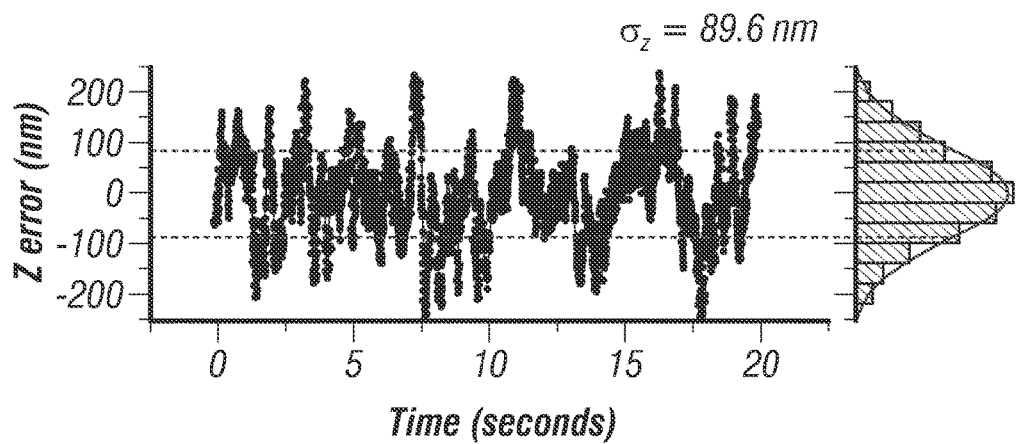

The localization precision stayed below 45 nm when the particle speed was less than 8 μm/s (see FIG. 7b). It should be noted that the fastest molecular motor known today, FtsK, travels at about 7 μm/s [28]. Other than prescribed motions, the inventors also tracked freely diffusing particles at various diffusion rates. Diffusion coefficients were estimated from fitting the mean-square displacement (MSD) and compared with the values predicted from the Stokes-Einstein equation. Excellent agreements were seen in a wide range of diffusion coefficients (0.07-4.3 μm2/s in FIG. 7). Whereas a previous 3D-SPT report has successfully tracked particles diffusing at 20 $\mu m^2/s$ [14] it was noted that the diffusion coefficient of a free receptor complex on the cell membrane is roughly on the order of 0.02 μm2/s [29] and the fast diffusion coefficient of proteins in cytosol is on the order of 5 μm2/s [30]. The system thus was able to probe rapid molecular transport dynamics inside cells.

Temporal Resolution Characterization

Temporal resolution of the disclosed tracking system is defined as how fast the particle position is discerned in 3D space with reasonable localization accuracy. Although the control loop period for the disclosed systems is 1-5 ms, it is noted that the temporal resolution can be significantly better than 1 ms by outputting the individual photon event data (Time Tag) from the TCSPC board (while the control loop period remains at 1-5 ms). In offline analysis trajectories can be resampled with temporal resolution down to 50 μs (see FIG. 11). In this condition the trajectory is plotted from a combination the original control loop rate voltage outputs and n-samples of higher time resolution localizations relative to the current beam position. Localizations are performed using re-binned histograms with photons arriving only within the super-sampled time period.

Figure 11A:
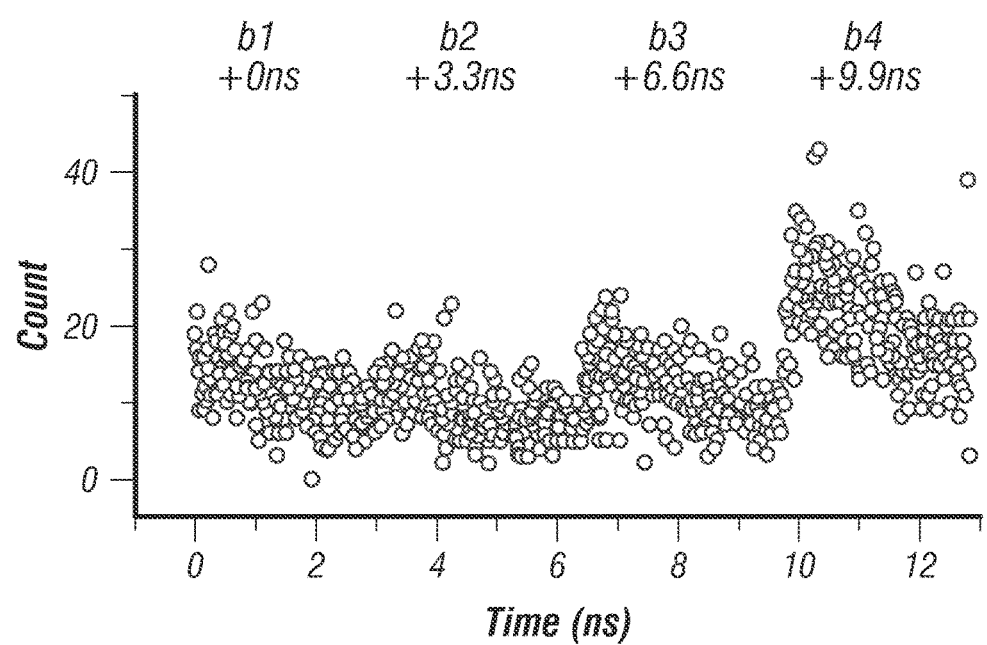
FIG. 11 shows data relating to an example photon count histogram.
Figure 11B:
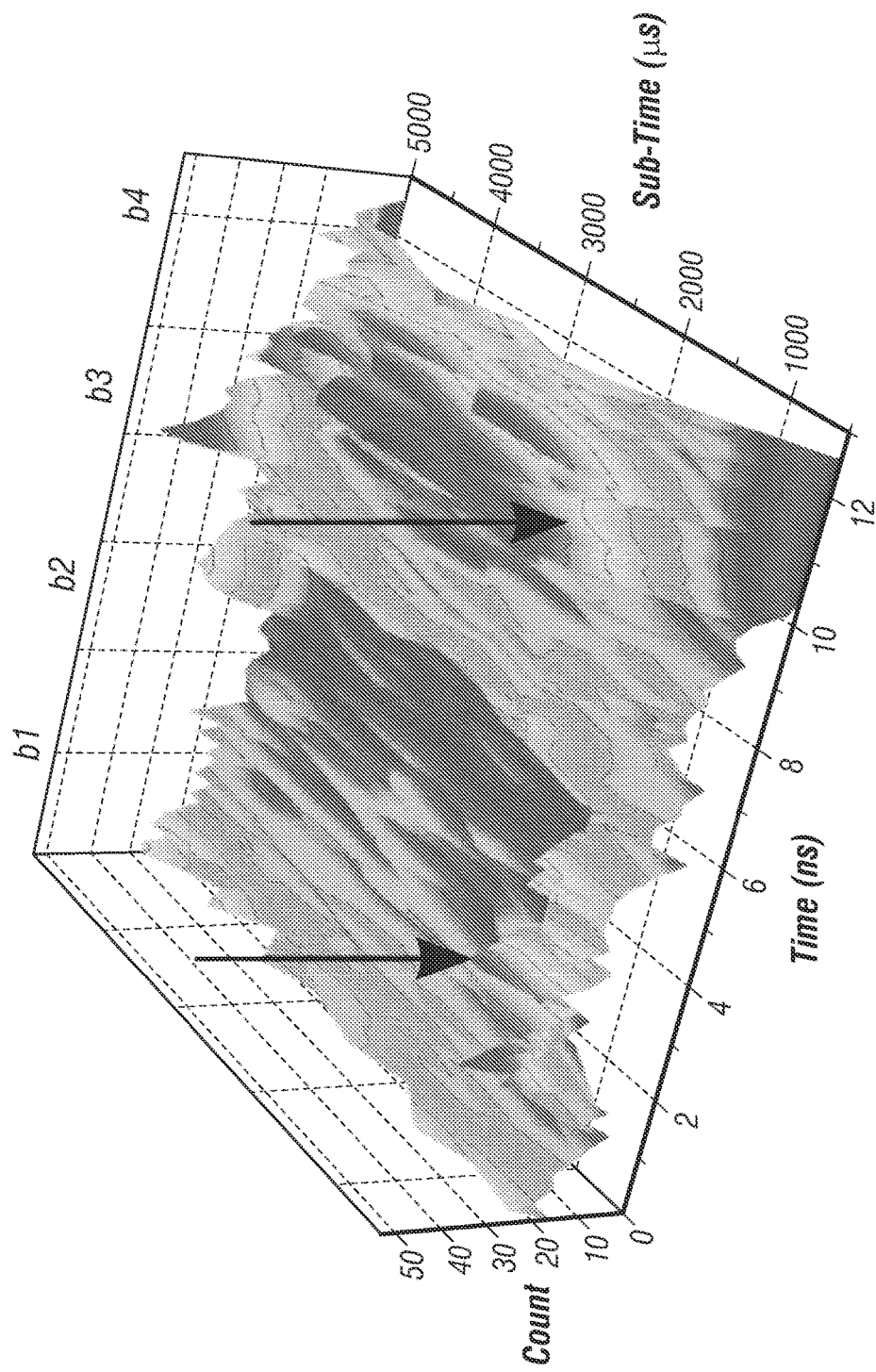
Figure 12A:
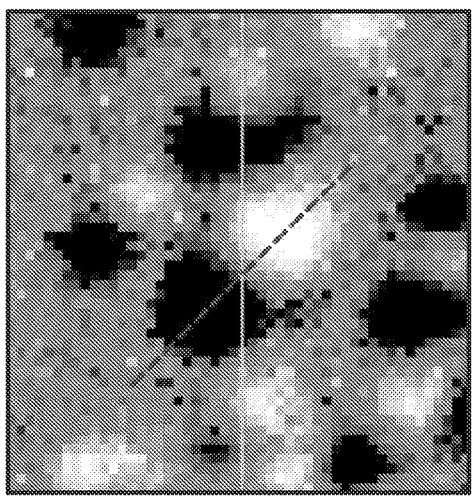
FIG. 12 shows data relating to molecular detection function.
Figure 12B:
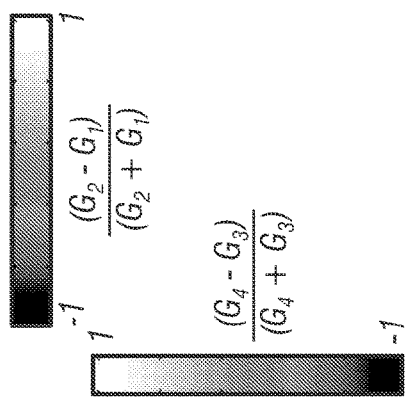
Figure 12B:
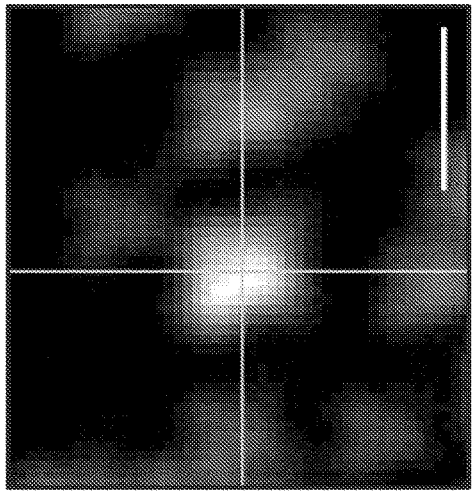
Figure 12C:
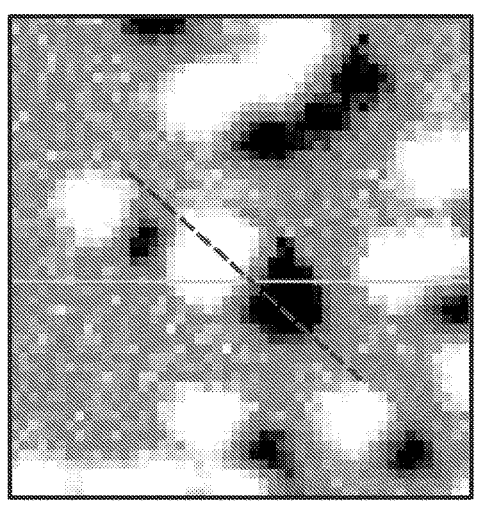
Figure 12D:
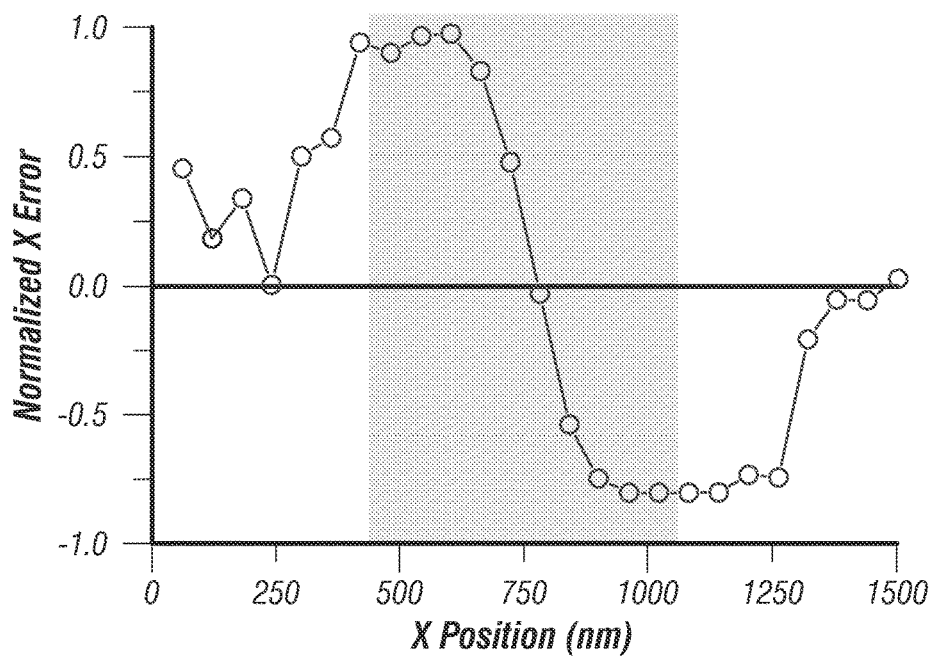
Figure 12E:
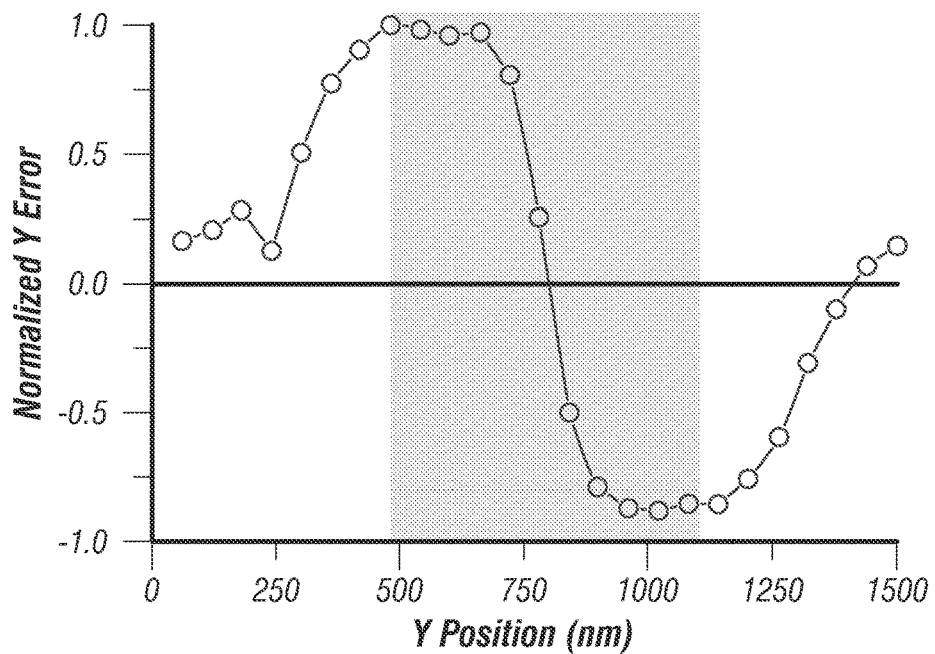
Figure 12F:
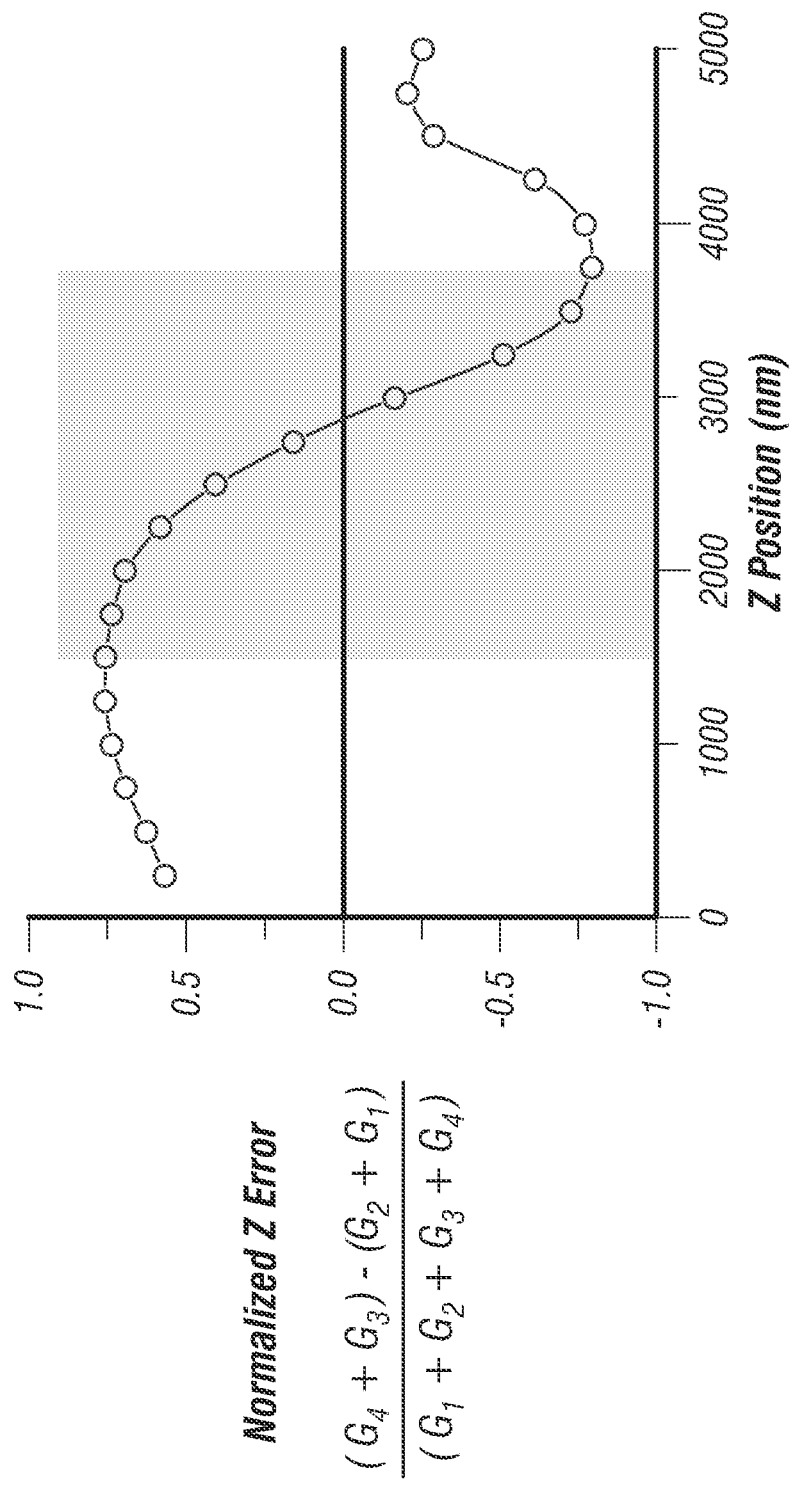
Figure 13A:
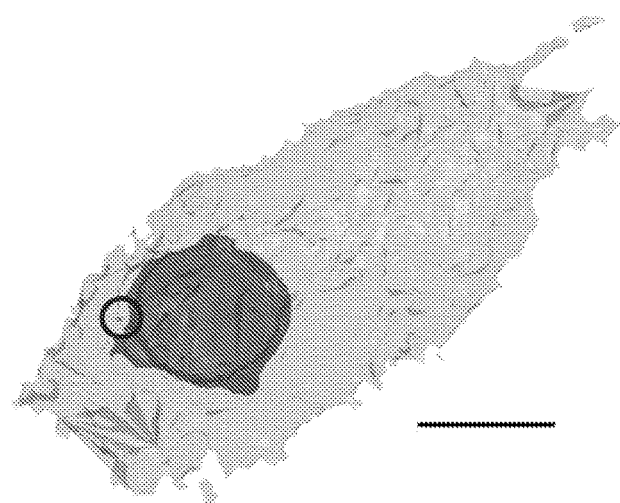
FIG. 13 shows data relating to 3D single particle tracking in monolayer cell cultures.
Figure 13B:
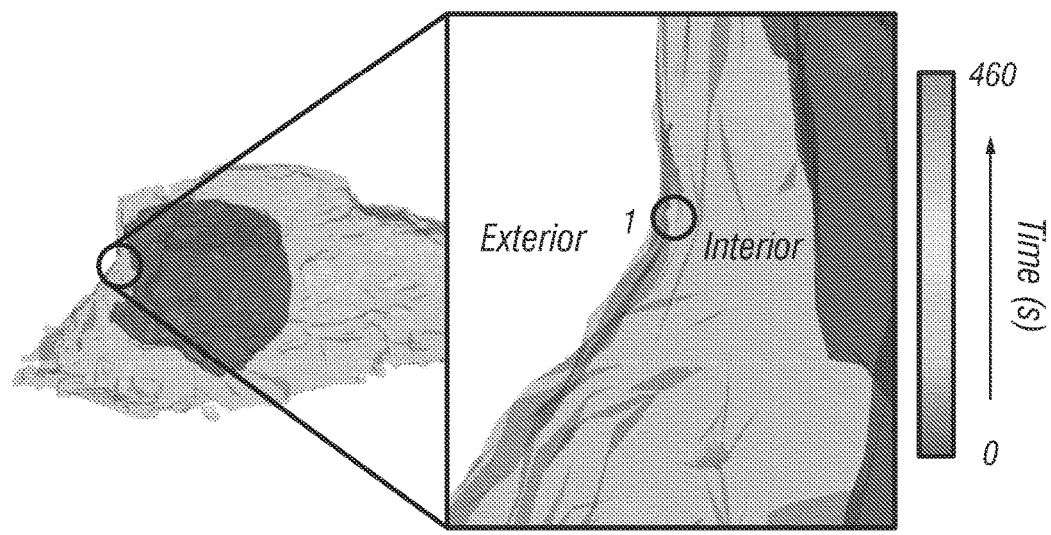
Figure 13C:
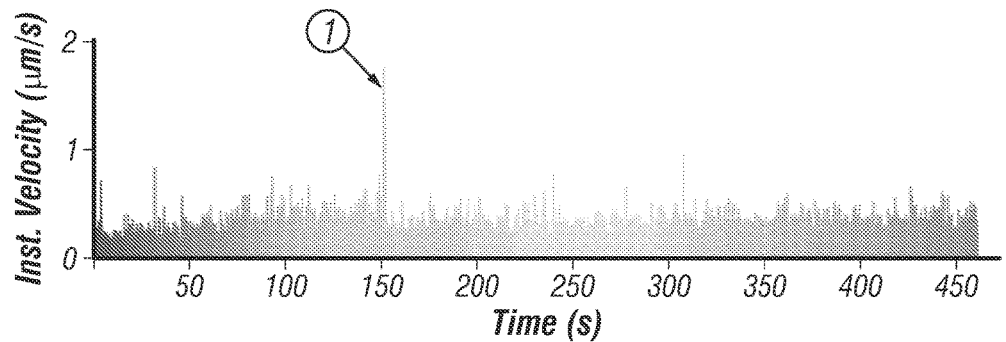
Figure 13D:
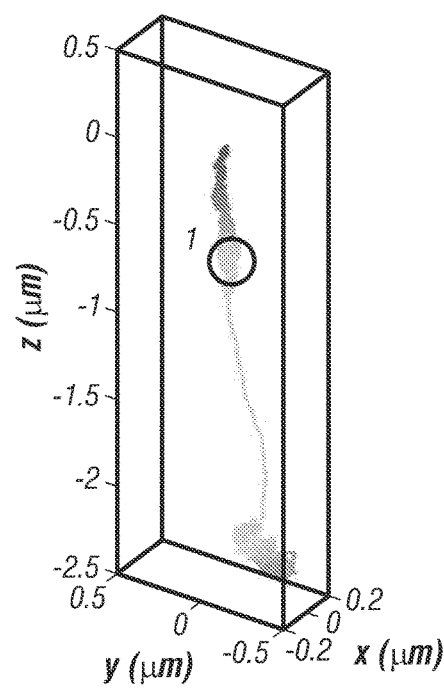

FIG. 11 shows 50 is time resolution. To demonstrate resolution down to 50 μs bright nanoparticle trajectories were measured and reconstructed using individual photon count data (see Section titled Online Methods). 40 nm diameter fluorescent microspheres (F8770, Life Technologies) were tracked in a 50% wt. glycerol solution under free diffusion. The individual photon count data stored in the FIFO was saved and analyzed in post-processing to reconstruct trajectories with higher temporal sampling. Using sufficient laser power (3 mW/beam) a photon count rate between 1-2 MHz was achieved, which corresponds to between 50-100 photons per localization at 50 μs time resolution. The inventors were able to localize the particle with this number of photons as useful signal counts for each beam are 12-25 photons whereas background noise, even in the worst condition, is only 0.5 photons per beam (for 40 kHz background during live cell imaging). FIG. 11a shows an example photon count histogram sampled from a single control loop period of 5 ms. FIG. 11b shows the same photon count data resampled with 200 μs time bins and displayed as a 2D surface, x-axis is the micro-time in nanoseconds and y-axis is the resampled histogram time with 200 μs resolution. The black arrows denote a sudden shift in beam intensities resulting from the particle movement during the 5 ms integration period. A perfectly centered and stationary particle would appear as four ridges along they axis of the 2D surface. FIGS. 11c, 11d, and 11e show a 0.5 second long trajectory sampled with 5 ms, 100 µs, and 50 µs time resolution, respectively.

Tracking Depth Characterization

To mimic 3D tracking in a turbid tissue sample, 40 nm diameter fluorescent beads were fixed within a 9% gelatin gel with 1% intralipid as shown in FIG. 8.

FIG. 8 shows localization uncertainty through turbid media. FIG. 8a shows 40 nm diameter fluorescent beads (F-8770, Life Technologies) were prepared in a matrix of 1% Intralipid and 9% gelatin to mimic a turbid tissue sample. Directed motion was performed as described previously (FIG. 10) with an independently controlled 3D piezo stage. FIG. 8b shows helical directed trajectories were measured at three different depths all with a mean velocity of 1.0 µm/s. Trajectories were recorded at 10 µm, 100 µm, and 200 µm past the coverslip. As expected required excitation power increases with increasing depth, while localization accuracy decreases. X and Y localization suffer only a minor decrease, from about 16 nm to about 21 nm rms whereas the Z localization experiences a slightly increased reduction in precision from about 60 nm to about 89 nm rms. This reduction in Z localization can be attributed to an elongated PSF that occurs when light is focused through scattering samples that effectively blurs the beams along z and lowers the optical contrast signal required to lock onto the target. FIGS. 8c, 8d and 8e show localization error values recorded at 200 µm depth for x, y, and z dimensions respectively. Histograms are displayed to the right for each curve. It can be seen that these distributions can be fit very accurately to a normal distribution indicating that there are no systematic errors or instrument artifacts corrupting the localization even at a depth of 200 µm into the scattering sample.

When tracking beads undergoing prescribed motion at about 10 µm depth, localization uncertainty stayed the same in x-y direction but slightly increased in z direction (60 nm). Localization uncertainty further increased to about 89 nm at the depths of 100 through 200 µm, while localization uncertainty stayed below 22 nm in x-y direction at both depths. This reduction in z localization precision may be due to an elongated molecular detection function (see FIG. 12) that occurs when light is focused through scattering samples which may blur the beams along the z dimension [31] and lower the optical contrast signal required to lock onto the target. Despite this slight reduction in z tracking accuracy at depth, TSUNAMI is capable of maintaining better than 100 nm axial localization through 200 µm of a scattering sample.

FIG. 12 illustrates molecular detection function. To calibrate the 3D localization technique 100 nm diameter fluorescent beads were fixed to a coverslip and imaged in 3D in a 3 by 3 by 5 µm stack. At each voxel of the stack a photon counting histogram was recorded using 5 ms integration time. The raw waveform was demultiplexed (see discussion of FIG. 3) and processed to yield error values along all three dimensions. FIG. 12a shows the composite image of all 4 beams at the mean z focus. Blue lines denote the center x and y axes. FIG. 12b shows the X error map which is a calculation of x error weight Ex at every pixel in the image. FIG. 12c shows the Y error map which is a calculation of the y error weight, Ey, at every pixel in the image. FIG. 12d shows a line profile through the x error map at the location drawn in FIG. 12b. Precision target tracking is feasible over a 500 nm range. FIG. 12e shows a normalized error line profile through Y error map (FIG. 12c) showing near exact positional dependence on error as the x profile, as expected. FIG. 12f shows the normalized error through all images in the stack located at the mean intensity position denoted by the intersection of the blue lines in FIG. 12a. To smooth the curve the error value was calculated with 2 adjacent pixels in each image, the slope remains the same. Scale bar is 1 µm.

2P-3D-SPT in Monolayer Cultures and Cancer Spheroids

FIG. 13 shows 3D single particle tracking in monolayer cell cultures. The capability to track singly labelled EGF molecules is demonstrated in a high background live cell environment. FIG. 13 a shows 3D Isocontour model of the cell structure with staining for plasma membrane (red) and nuclei (blue). Scale bar is 10 µm. FIG. 13b shows cell iso-surface model plotted with trajectory overlaid (inset: Zoomed in view of the particle trajectory, a single fluorescence microsphere labelled EGF molecule was tracked for a duration of 460 seconds with rainbow coloration corresponding to time, where blue marks the beginning). FIG. 13c shows instantaneous velocity graph with colors directly corresponding to the trajectory. For the first 150 seconds the particle undergoes slow directed diffusion (mean velocity ~0.4 µm/s) along the exterior of the cell. A ramp in velocity is observed followed by a period of high average velocity (start denoted as point 1), ~2 µm/s, and unidirectional transport of 1 µm. This behavior indicates some form of internalization into the cell or transport within the cell. FIG. 13d. Trajectory plotted with no cell contour overlay.

Figure 14A:
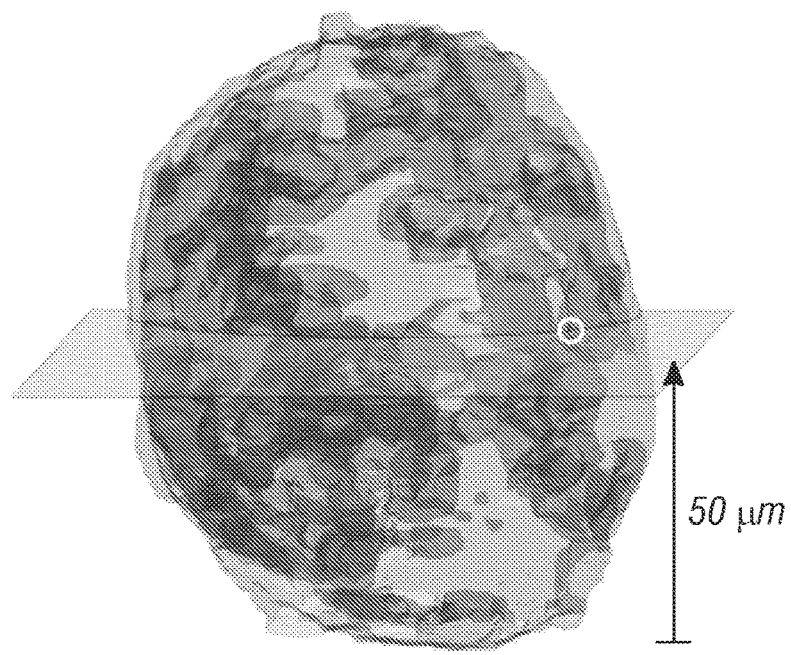
FIG. 14 shows data relating to deep single particle tracking of EGFR in a spheroid model.
Figure 14B:
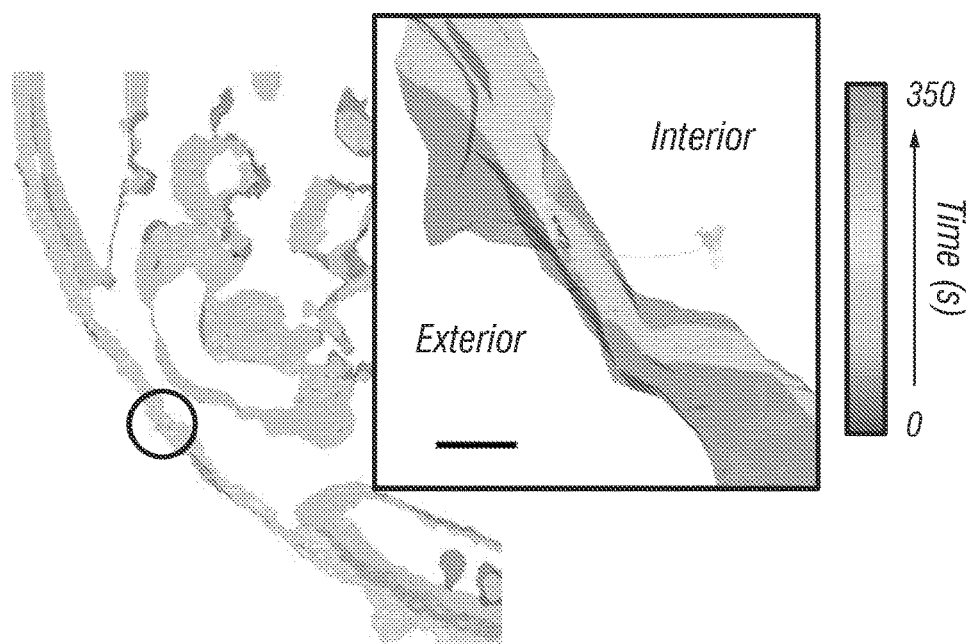
Figure 14C:
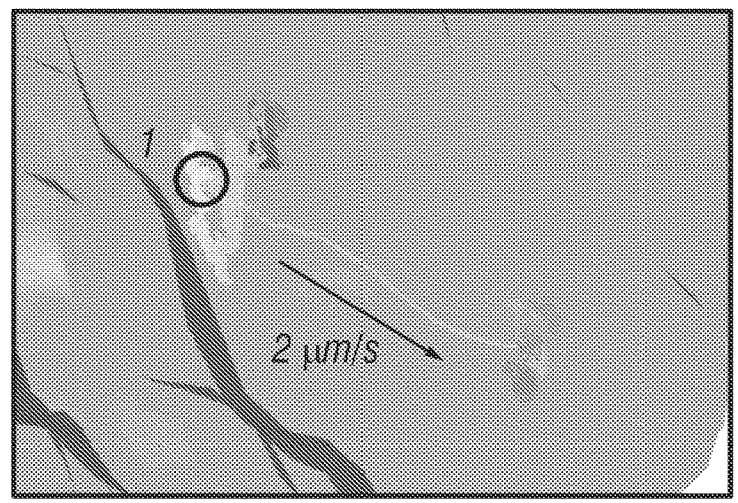

Here the inventors used the endocytosis and subcellular trafficking of EGFR complexes in A431 monolayer culture and tumor spheroids as a model system for instrument validation. The inventors tracked single nanoparticle bound EGFR complexes (see section titled Online Methods) in monolayer cell cultures (see FIG. 13A) and spheroids with a diameter of about 100 µm (see FIG. 14a) for periods up to 10 minutes. Prior to SPT, two photon fluorescence images were taken of the surrounding cellular environment. Staining of the plasma membrane and nucleus allows co-registration of the particle trajectory and cellular landmarks. In post processing the trajectory and cellular images are co-registered (see FIG. 13B) to visualize EGFR entry pathways.

The inventors found that out of 100 trajectories about 80% of EGFRs had been internalized into the cells within approximately 6 minutes. The inventors notice transport modes similar to those described in prior work (32) (see FIG. 13d). The average velocity (2 µm/s) and total transport length (1-2 µm) during internalization are in good agreement with values previously reported.

FIG. 14 shows deep single particle tracking of EGFR in a spheroid model. FIG. 14a shows 3D isocontour of a 100 µm diameter spheroid taken with 2P LSM staining for plasma membrane (red) and nuceli (blue). The highlighted slice denotes the z-plane (at 50 µm depth) where the trajectory was measured. The white circle denotes the location of the trajectory on the plasma membrane. FIG. 14 b shows the isocontour model of the ±5 µm slice taken 50 µm deep within the spheroid. The cell membrane and nuclei are overlaid with the trajectory (black circle), (inset: zoomed view of the trajectory). The trajectory begins inside the cell with slow displacement (velocity about 0.17 µm/s) for 250 seconds where velocity increases to 2 µm/s and is sustained for 0.5 seconds in a unidirectional manner. This behavior is indicative of some form of internalization. FIG. 14c shows a close view of the trajectory. Point 1, marked with a black circle, is where velocity increases and is sustained for 0.5 seconds. FIG. 14d. shows the trajectory plotted without cell overlay, the total transport length within the high velocity region is 1 µm. FIG. 14e shows instantaneous velocity plot over the duration of the trajectory. Scale bar is 600 nm.

Figure 14D:
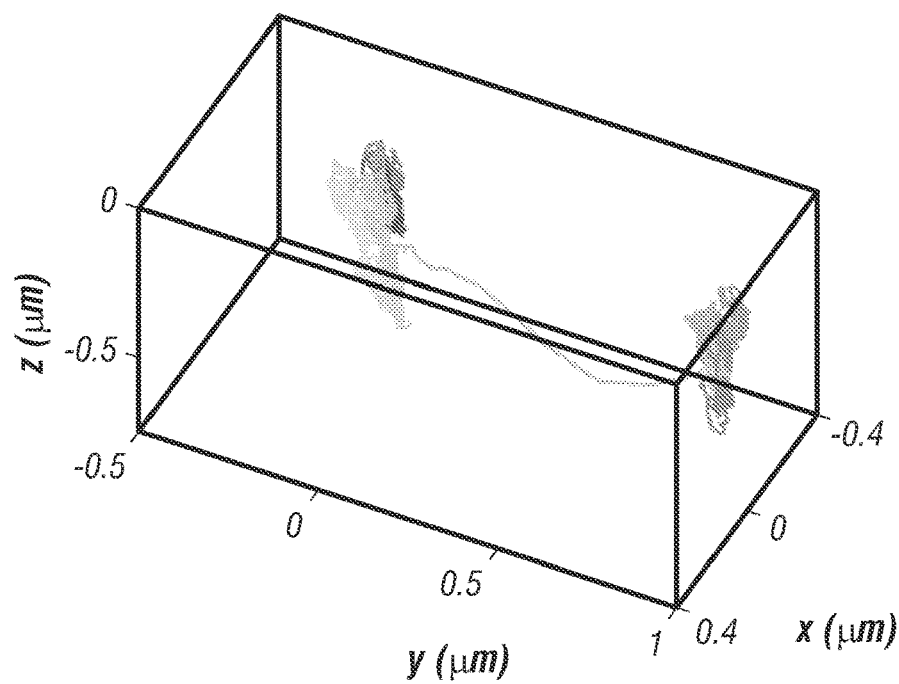
Figure 14E:
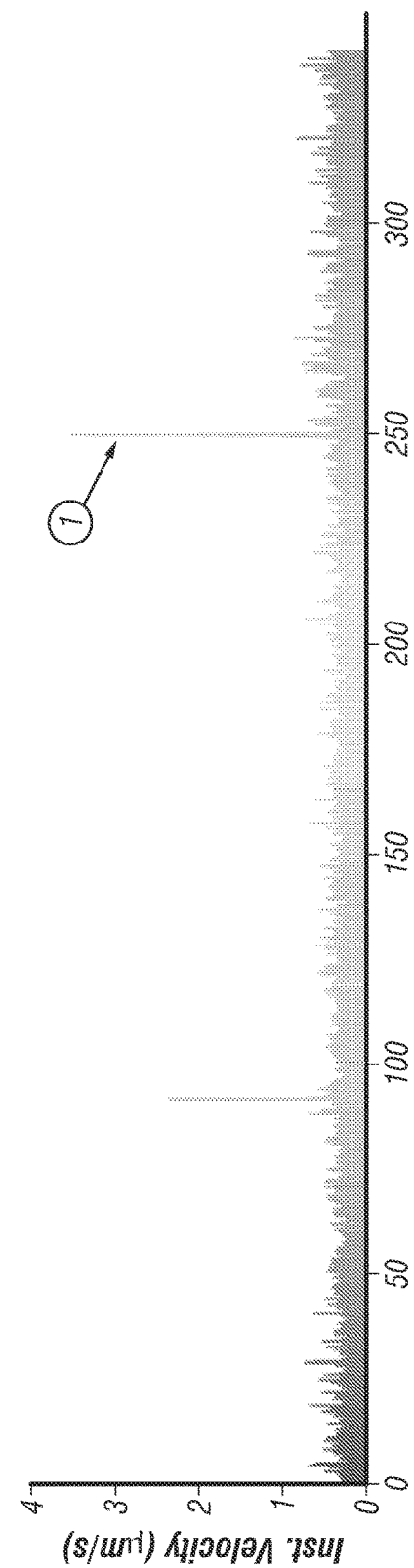
Figure 15A:
FIG. 15 shows data relating to an inhibited spheroid trajectory.
Figure 15B:
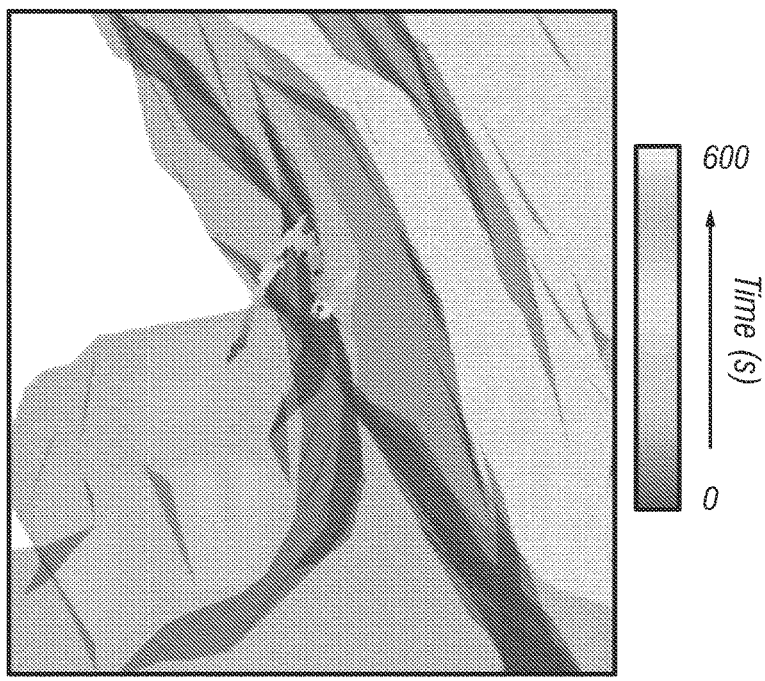
Figure 15C:
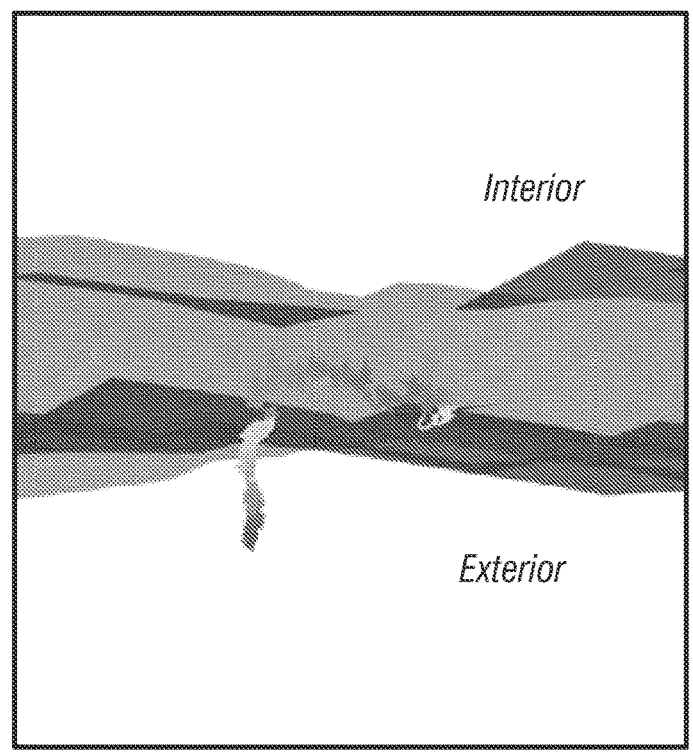
Figure 15D:
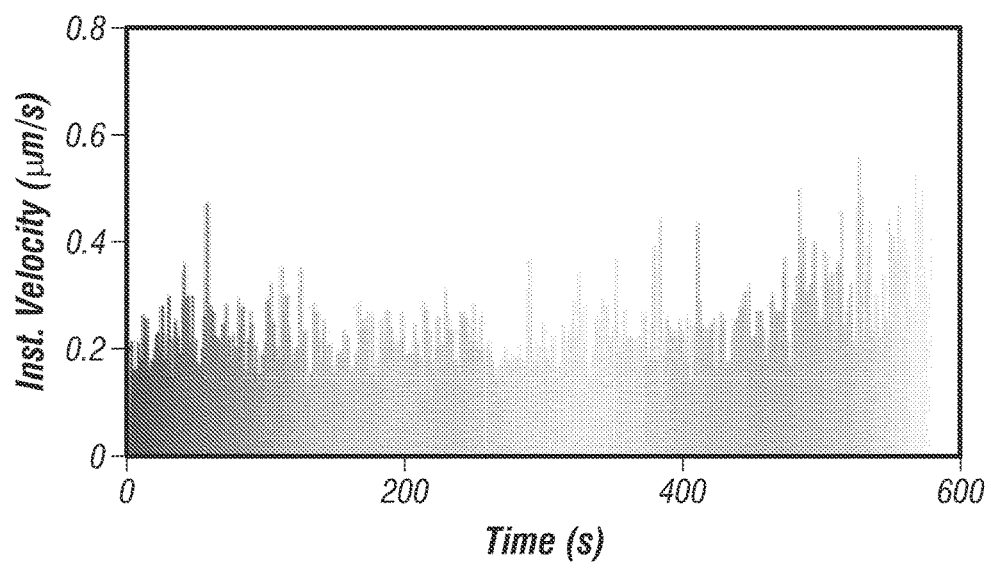

For spheroid models the inventors measured EGFR entry pathways at a variety of depths from 20 µm to 100 µm past the coverslip (see FIG. 14c) and found good agreement in terms of the speed and transport length during internalization (see FIG. 14d). Although the required power to obtain clean spheroid images expectedly increased with imaging depth, the total signal count rate (500-800 kHz) and signal to noise remained well within a threshold required for target locking. EGFR trajectories were easily measured at a depth of 100 μm for up to 10 minutes with minimal photobleaching. To evaluate whether the trajectories are representative of biological events or system artifacts the inventors measured trajectories under a control environment with an endocytosis inhibitor, sodium azide, and low temperature (<20° C.) (see FIG. 15). Of the 30 inhibited trajectories the inventors observed no high speed transport modes and only external membrane bound slow diffusion with an average velocity of about 0.2 μm/s. The average tracking duration was 500 seconds.

FIG. 15 shows an inhibited spheroid trajectory, specifically an example EGF trajectory with sodium azide inhibitor in a spheroid model. FIG. 15a shows an isocontour image with cell membrane (red) and nucleus (blue) are overlaid with the trajectory (black circle). FIGS. 15b and 15c shows zoomed images of the trajectory. Over the entire 600 second trajectory the displacement was about 600 nm and no entry through the membrane occurred. FIG. 15d shows instantaneous velocity plot with mean velocity 0.2 μm/s.

The disclosed methods and systems are capable of measuring biologically relevant activity in the high background environment of monolayer and spheroid models with instantaneous transport speeds up to 7 μm/s. The inventors believe that TSUNAMI is capable of measuring EGFR translocation pathways at depths 10 times what was previously possible through highly scattering, cell dense samples. In addition the multi-color, multi-resolution two photon fluorescence imaging functionality is inherently integrated to allow for co-registration of deep trajectories to local cellular/tissue environment in three dimensions.

Discussion

Whereas a few reports demonstrated 3D-SPT in monolayer cell cultures using two-photon excitation [2,18] to the best of the inventors' knowledge high-resolution subsurface particle tracking in three dimensions has never been demonstrated in highly scattering multicellular environments. One recent report demonstrates deep 3D-SPT light sheet microscopy using astigmatism [33] however the capability is limited by the use of an emCCD (16 ms temporal resolution), and would prove difficult to implement multicolor tracking or simultaneous lifetime measurement schemes. Furthermore, the inventors expect an astigmatic PSF would have significantly decreased localization precision when tracking at depth (>10 μm) [17].

Other than penetration depth, two photon excitation provides the ability to excite multiple fluorophores simultaneously, which greatly facilitates multi-color detection (see FIG. 13). Two factors that determine the fundamental limit of the temporal resolution are the detector and the tracer. The timing resolution (FWHM of the instrument response function) of the disclosed detector (H7422P-40, Hamamatsu) is about 230 ps (see FIG. 6). Whereas this response time is typical in photon-counting detectors, it is still orders of magnitude faster than CCD. It is well known that localization accuracy of a fluorescent particle relies heavily on the brightness and photostability of this fluorescent molecule. Assuming that a bright fluorophore has an emission rate of $10^8$ s$^{-1}$ and 10 percent of emitted photons are collected, the detected photons could exceed $10^7$ per second. As approximately 100 photons are needed for particle position determination with moderate precision, this could mean that the ultimate temporal resolution for SPT is approximately 10 μs. Other research groups have reported achieving 10 nm 3D localization precision and 10 μs temporal resolution in confocal 3D tracking of a giant QD cluster (about 40 QDs) [14]. The 3D tracking of the currently disclosed system approach has better collection efficiency due to non-descanned detection and the emission light is not split among multiple detectors. Accordingly, the currently disclosed system should reach similar temporal resolution and localization precision using a tracer system with ultrahigh emission rate but with a short lifetime.

Moving the beam through the sample instead of moving the sample itself [14,15,21] has the additional advantage that beam steering is generally faster than the movement of a potentially heavy stage. Also steering the beam is particularly suitable for applications in neuroscience, such as patching clamping, which requires stationary samples. While the stage response frequencies (10 kHz for the galvo mirrors and 300 Hz for the objective z-piezo stage) do not determine the temporal resolution of the currently disclosed tracking system, they impose an upper limit on the observable particle speeds. One way to bypass this limitation in mechanical scanning and negate the possibility that the observed dynamics are influenced by the objective motion (via mechanical coupling through the immersion medium) is to use fast adaptive optical elements in both lateral scan [21,34] and axial focusing [35].

An important characteristic of the currently disclosed tracking microscope lies in the fact that it is readily compatible with a number of fluorescence spectroscopy or microscopy techniques for probing molecular interactions at the true single-molecule level and in real time, including FRET36 (via lifetime measurements), multi-color single-molecule imaging/spatiotemporal colocalization analysis [37] step counting [38] and MSD analysis [34]. Since only one detector is used for 3D tracking, additional detectors can be easily added and used for simultaneous, multi-color detection, which can provide a structure overview of the particle's surrounding environment or indicate molecular interactions. On the other hand, it is not straightforward to detect the second color simultaneously on the traditional confocal tracking setups that employ 3-5 detectors for spatial filtering [14-16] as twice as many detectors and serious alignment effort may be required for multi-color detection.

Here the inventors demonstrate a new 2P-3D-SPT microscope (TSUNAMI) that addresses fundamental limitation of deep and high-resolution single-particle tracking in the 3D space. Extended from the current tracking results in multicellular models, the inventors are working towards direct in vivo 3D-SPT at high spatiotemporal resolution. The currently disclosed methods and systems can allow researchers to explore new questions in receptor transport and dynamic processes directly in 3D tissues.

Figure 9A:
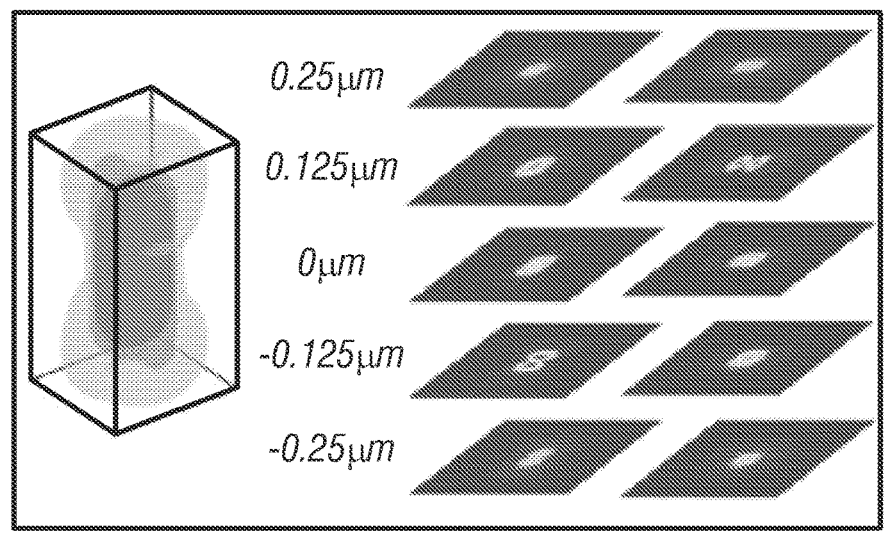
FIG. 9 shows data relating to a comparison of molecular detection functions.
Figure 9B:
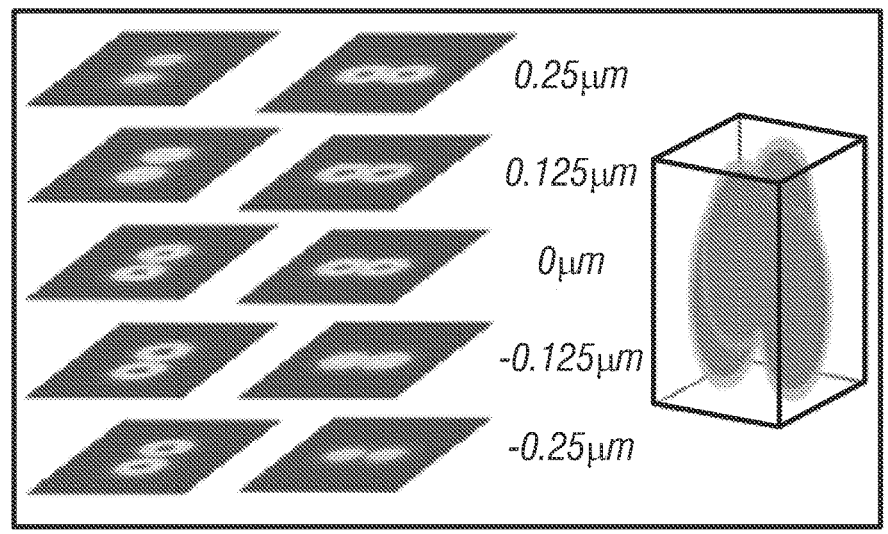
Figure 9C:
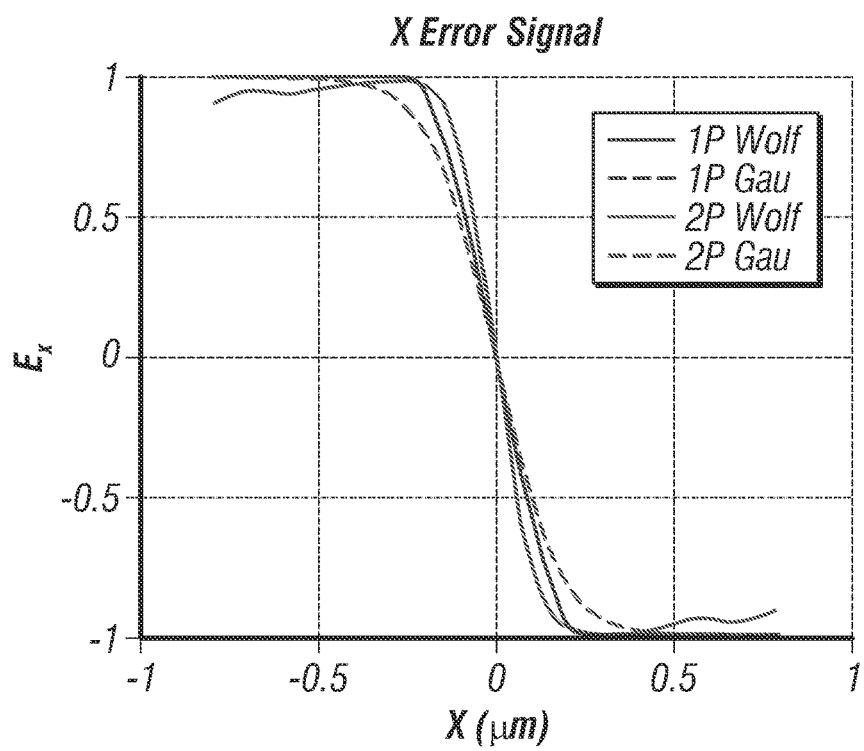
Figure 9D:
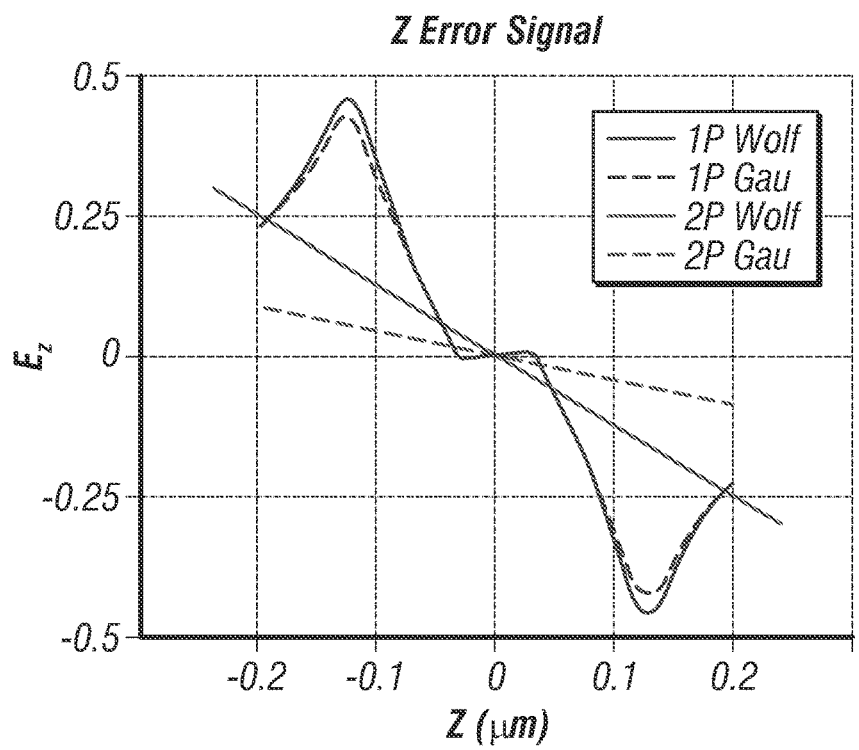
Figure 10C:
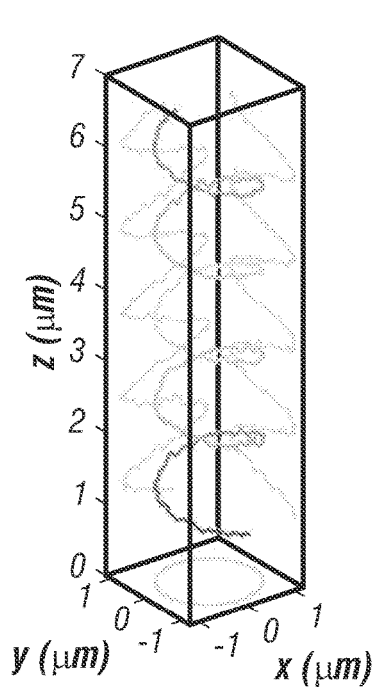
FIG. 10 shows data relating to a localization uncertainty measurements
Figure 10C:
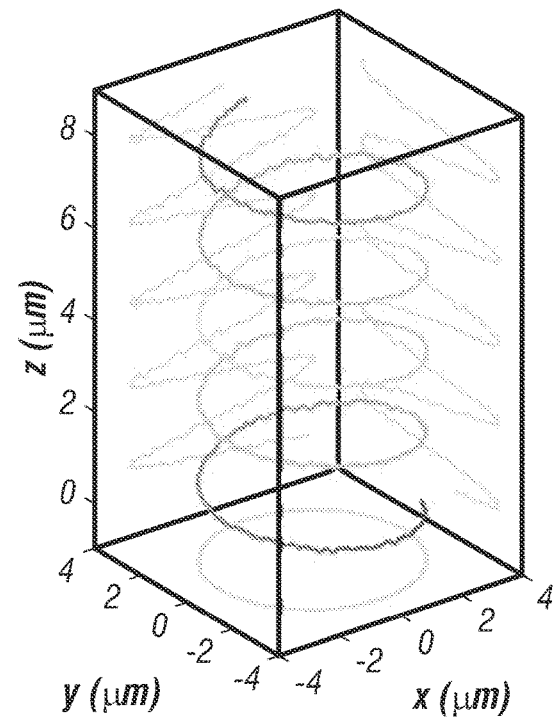
Figure 10C:
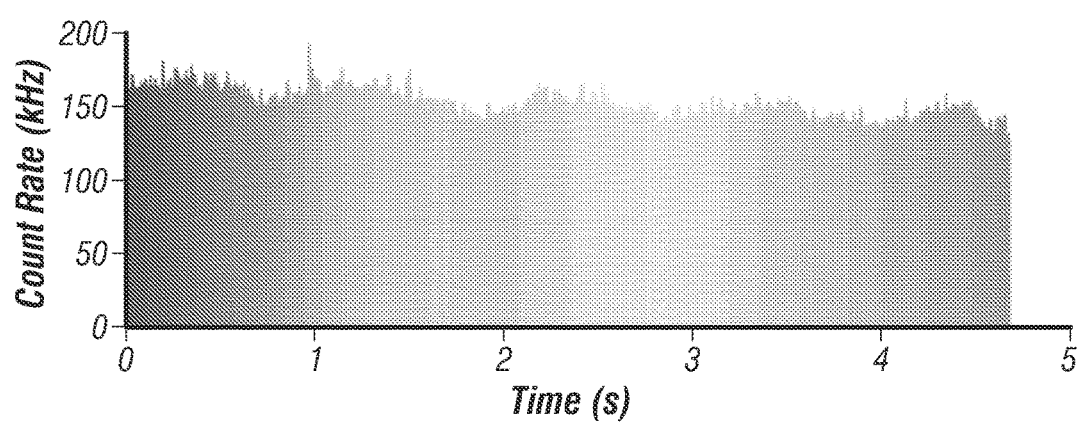
Figure 10D:
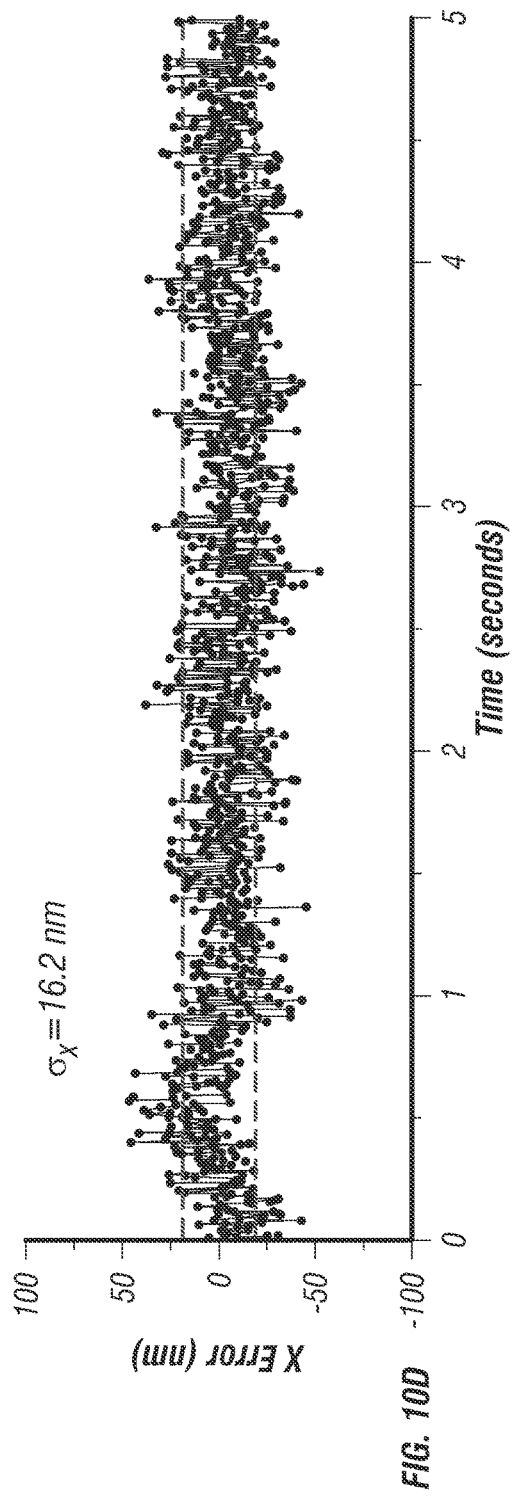
Figure 10E:
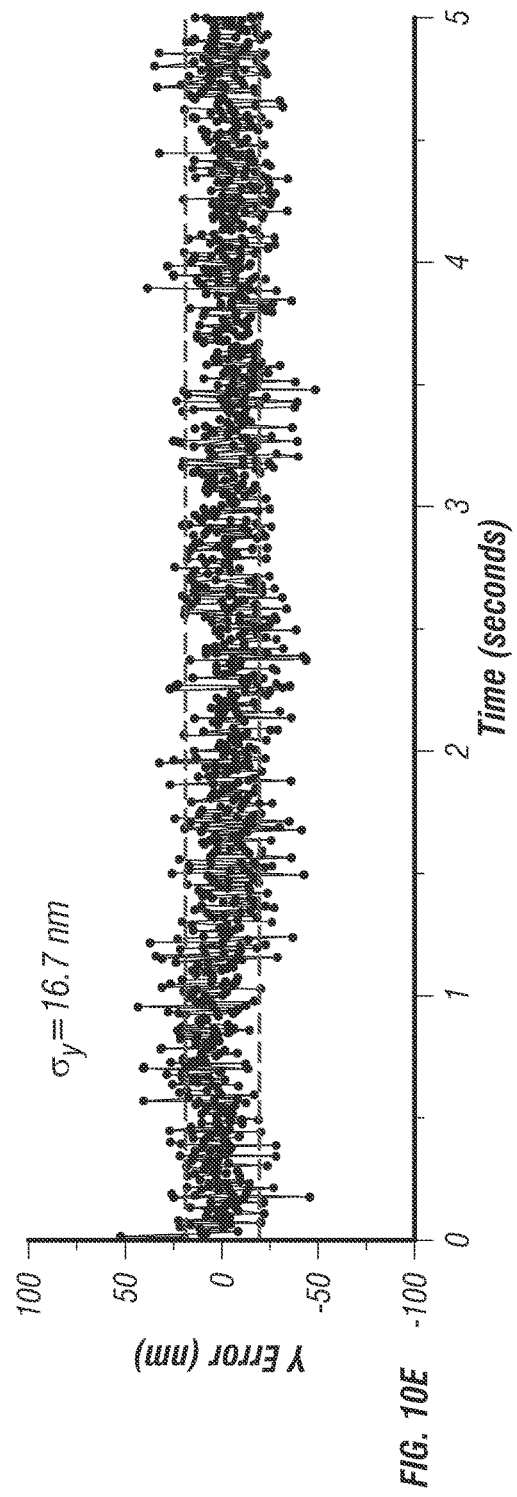
Figure 10F:
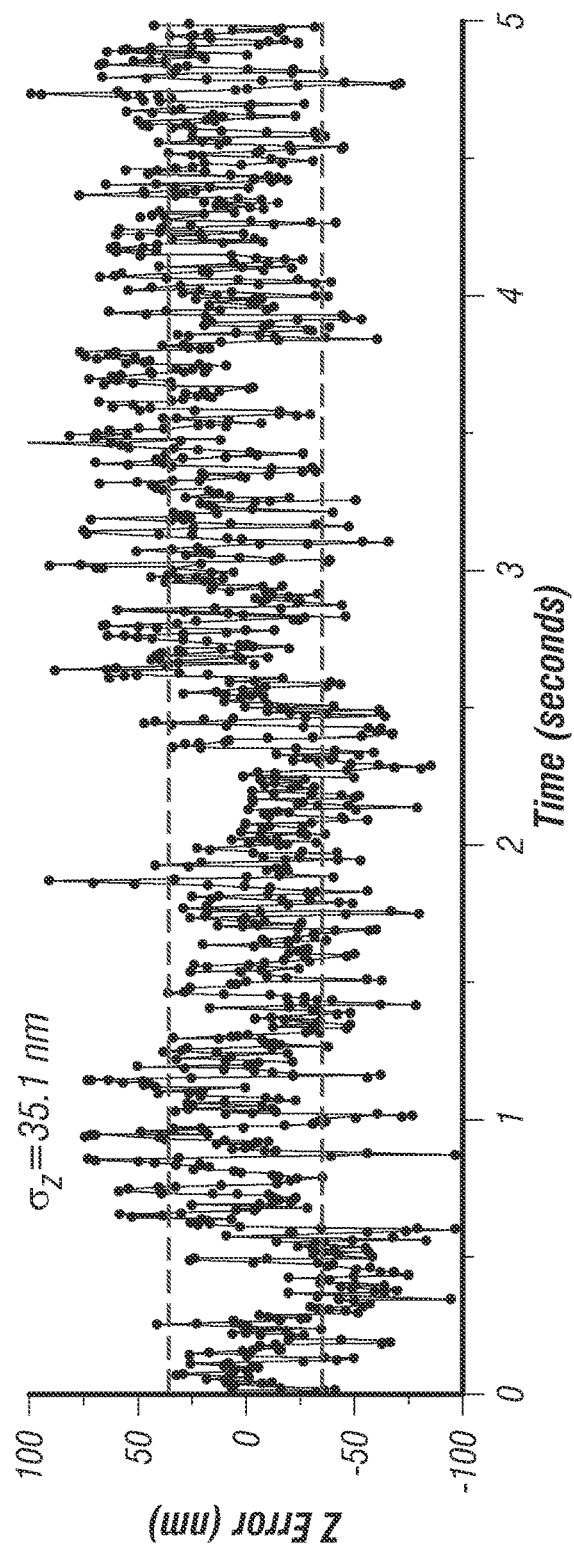
Figure 16:
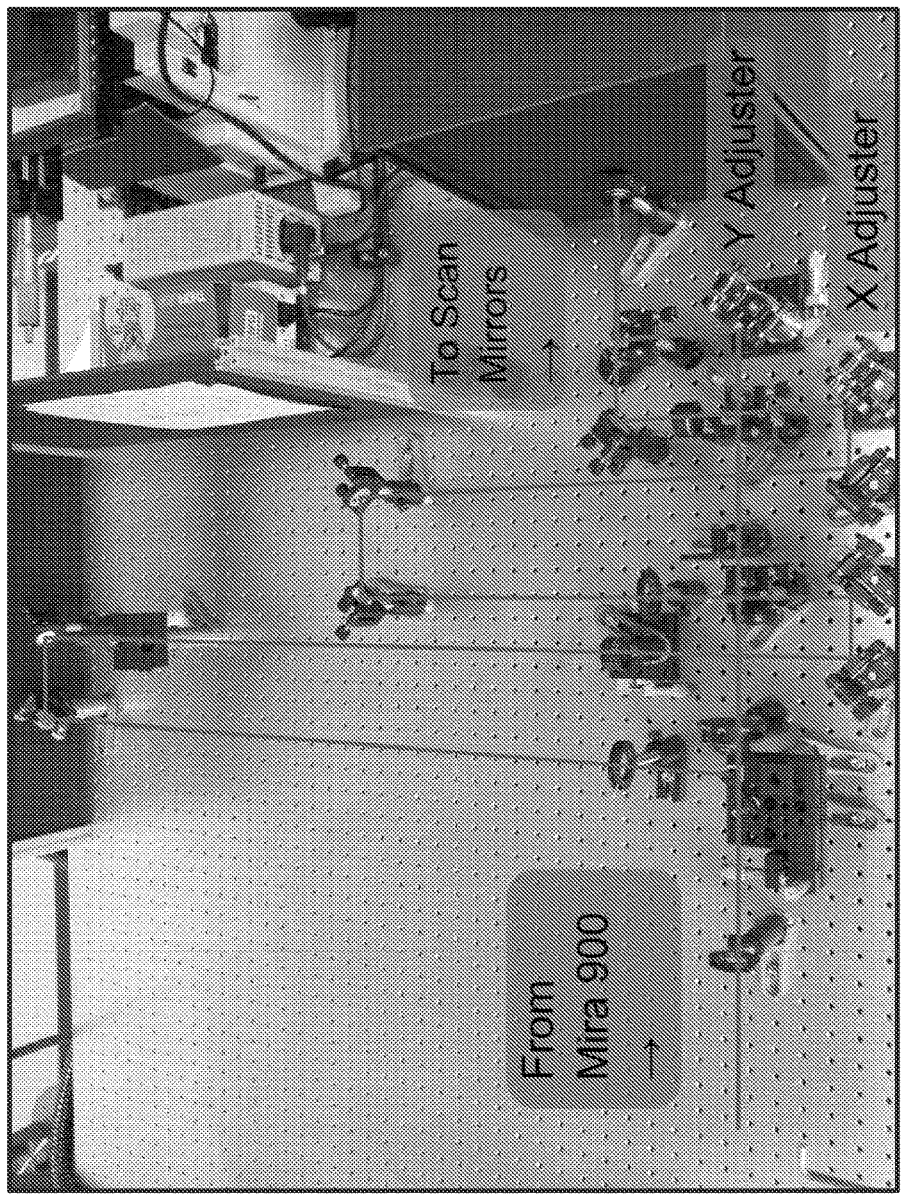
FIG. 16 shows a photograph of a spatiotemporal beam multiplexer according to exemplary embodiments of the present disclosure.

Online Methods 2P-3D-SPT instrumentation. The spatiotemporal beam multiplexer shown in FIG. 5) is created entirely from passive optics comprised of beam splitters, mirrors, and waveplates (see FIG. 16). A single pulse train from a modelocked Ti:Al2O3 laser (Mira 900, Coherent) tuned to 835 nm is used as the primary beam which then gets multiplexed into four beams offset in time and space. For temporal offsets, it was determined that to equally space four beams with an original 76 MHz repetition rate the delay time must be 3.3 ns which corresponds to approximately 1 m physical path length. For spatial offsets each beam is first coaligned onto the primary optical axis. Adjusters which control x and y offsets are moved until a lateral spacing of approximately 500 nm is achieved in the image plane. Alignment repeatability is verified by projecting fiduciary marks onto the LSM image during alignment such that each beam's center is aligned to the same point in space to sub-100 nm repeatability. Axial spacing is controlled using a telescope assembly placed in the optical path of one beam pair to adjust their collimation. The alignment of axial spacing is verified using molecular detection function 3D scans (see FIG. 12) until a spacing of 1 μm is achieved (see FIG. 9). Following the optical multiplexer the beams pass through a galvo scanning system (6125H, Cambridge Technology), before being focused through a 60×1.3 NA silicone oil objective (UPLSAPO60X, Olympus). FIGS. 9a and 9b show a comparison of molecular detection functions (MDFs). FIG. 9a shows that in the 1Photon-1Excitation-4Detector design (a confocal 3D tracking microscope system invented by J. Werner and coworkers) [15] the calculation indicated that the spatial resolving capability of MDFs fades away at a distance of 0.25 μm from the center of the MDFs (located at 0.125 μm), mainly due to the flattening of collection efficiency function (CEF) at this Z depth and a single excitation volume. As the spatial resolving capability disappears, target molecule will be lost. FIG. 9b shows that in the TSUNAMI design, the MDFs are dominated by the spatiotemporally demultiplexed two-photon excitation volumes, as the PMT has a large active area (i.e. CEF-1). FIGS. 9c and 9d show error signal comparison of 1P-1E-4D (blue curve) and TSUNAMI (red curve). Solid lines: Error signals derived from the Wolf excitation field expressions. Dashed lines: Error signals derived from the Gaussian-Lorentzian excitation expression. has the same dependence on y as on. The z-plane separation of the fiber input faces (projected into sample space) in 1P-1E-4D and z-plane separation of the excitation volumes in TSUNAMI are both set to be at 0.25 μm for comparison. The linear region of error signal is where the target molecule can be effectively tracked. is steeper than, meaning our tracking systems are more sensitive to XY displacement than Z displacement. As a result, the XY tracking accuracy is always better than the tracking accuracy in Z.

For a typical experiment the inventors use an average laser power of approximately 2 mW per beam (8 mW) total at the objective back aperture. For a typical 40 nm diameter fluorescent bead (F8770, Life Technologies.) photon count rates are in the range of 500-800 kHz and targets can be tracked for durations up to 10 minutes. Background fluorescence signal is on the order of 3 kHz which includes a 150 Hz background signal from the detector. Signal-to-noise ratios are typically above 20.

Demultiplexing Emission Signal

Demultiplexing of fluorescence emission can be done by time resolving the excitation contributions of each of the four multiplexed beams with fast photon counting electronics. The fluorescence signal detected is an interwoven stream of photons excited by all four excitation beams. That signal can be time gated with 3.3 ns increments to effectively isolate the signal contributions from each beam and consequently isolate the signal contribution in space as well. Emission demultiplexing is done electronically via time-correlated-single-photon counting (TCSPC) analysis. Fluorescence signals are detected by a cooled GaAsP photomultiplier tube with 5 mm square active area (H7422PA-40, Hamamatsu) in non-descanned configuration.

The current output from the PMT is amplified through a 2 GHz cutoff bandwidth preamplifier (HFAC-26, Becker and Hickl GmbH) and sent into a photon counting board (SPC-150, Becker and Hickl GmbH) to be counted and correlated to the 76 MHz reference clock of the laser oscillator. Given the electronics setup the fundamental timing resolution is on the order of the instrument response frequency which was measured to be 230 ps FWHM (see FIG. 6).

Figure 6:
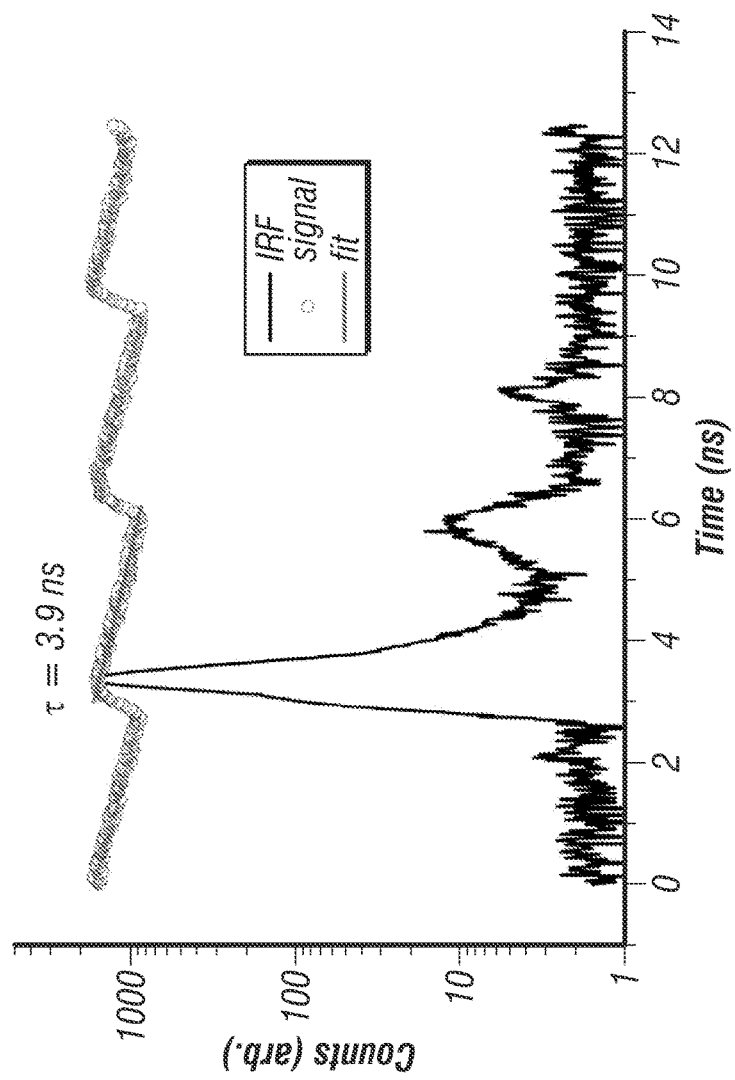
FIG. 6 shows data relating to fluorescent lifetime measurement during tracking.

FIG. 6 shows fluorescent lifetime measurement during tracking. Lifetime measurements can be simultaneously recorded during tracking by using every photon arrival event as described in FIG. 11. An example photon counting histogram with instrument response function (IRF) and lifetime fit overlaid. The photon histogram is an aggregate of 500 ms of data (100 loop cycles) recorded while tracking a single 40 nm diameter fluorescent microsphere (F8770, Life Technologies) in a 50% wt. glycerol solution under free diffusion. The lifetime decay rate was found to be 3.9 ns. Measuring the IRF with 2P excitation at 835 nm was performed with a previously described method 8. The IRF full width half-max was found to be 230 ps, and 1% peak intensity after-pulsing was observed, which is an unavoidable characteristic of the GaAsP photocathode PMTs used for this system.

Tracking Control Software

In certain embodiments, the tracking acquisition control loop is run in LabVIEW (National Instruments) on the Windows 7 operating system. Time resolved signals from the TCSPC board can be read into LabVIEW by two methods, (1) histogram mode and (2) FIFO (time-tag) mode. In histogram mode the TCSPC board performs on board histogramming of the photons detected during a single control loop period (5 ms) and sends the data to LabVIEW for processing into new control signals (see FIG. 3). In FIFO mode each photon event is recorded by the board and processed on the fly in the LabVIEW control loop. For a loop rate of 5 ms and typical particle count rate of 500 kHz this requires time binning 2,500 photons which are represented with 12-bit precision. This task is easily achievable with current computing hardware. The data on each photon event can be recorded for post processing and re-binning to achieve timing resolutions down to 50 is with sufficiently bright particles (see FIG. 11). Deterministic timing for the LabVIEW control loop is achieved by forcing the program to run on a hardware timed clock from a PCI based data acquisition board (PCIe-6353, National Instruments). Using this hardware timed loop method periods down to 1 ms can be requested with no missed cycles for up to 60 seconds. At 5 ms the timed loop can run indefinitely with no missed cycles up to 20 minutes.

Control signals are generated by taking the ratio of the summed photon counts in each of the 4 times gates. Following the below formulas, $$E_x = \frac{G_2 - G_1}{G_2 + G_1}$$

$$E_y = \frac{G_4 - G_3}{G_4 + G_3}$$

$$E_z = \frac{(G_4 + G_3) - (G_2 + G_1)}{(G_1 + G_2 + G_3 + G_4)}$$

Where G1, G2, G3, and G4 are the total photon counts in each time gate. Error signals Ex, Ey, and Ez are modified by a proportional controller before being sent out by the PCIe-6353 board as analog signals to their respective actuators (galvos for x and y, and objective piezo stage (P-726 PIFOC, PI) for z).

2P LSM for 3D Reconstructed Images of the Multicellular Models

To obtain cell membrane and nucleus outlines traditional 2P LSM images were taken prior to recording a trajectory. Image sampling was performed at a fixed 512×512 resolution with either 100×100 µm² or 50×50 µm² sizes. Stacks were taken with 0.5 µm spacing in the z dimension and saved to binary files in a custom written LabVIEW interface. Post processing was performed in Matlab (Mathworks, Natick Mass.). The images were median filtered prior to being segmented by a thresholding method. Segmented contours were plotted in an isocontour format and overlaid with the trajectory. Since the same analog output board and actuators are used for imaging and tracking, the two datasets are referenced to the same voltage scale and so can be overlaid with no computational errors introduced. Although it should be noted that 2P-3D-SPT provides super-resolution trajectories of a single emitter, but traditional 2P LSM is still limited by the diffraction of light approximately 400 nm resolution. The cell contour data is used as a coarse guide for endocytosis events, but future work will be directed towards improving the resolution of local environment scans to better elucidate the particle's interaction with the surrounding environment.

Sample Preparation

EGFR-overexpressed A431 skin cancer cell was purchased from American Type Culture Collection (ATCC) and cultured in DMEM (Dulbecco's Modified Eagle Medium, Cat. No. 11995-065, Life Technologies) supplemented with 5% FBS (fetal bovine serum, Cat. No. SH30071, Thermo Scientific). The cell cultures were kept in humidified atmosphere with 5% CO2 in air at 37° C. Single suspensions were prepared by mild enzymatic dissociation using a trypsin/EDTA solution. For EGFR tracking in monolayer culture, A431 cells were seeded onto 8-well chamber slides (Nunc™ Lab-Tek™ II Chamber Slide™, Cat. No. 154534, Thermo Scientific) with the cell density of 1×105 cells per well and allowed to adhere overnight.

Agarose-coated 96-well plates were used to cultivate A431 spheroids. Each well of a 96-well plate (Cat. No. 130188, Thermo Scientific) was coated with 50 µL sterilized agarose solution (1.5% (wt/vol) agarose (Cat. No. A9539-100G, Sigma-Aldrich) in DMEM). The spheroids were prepared as previously described 39 and the plates were incubated for 96 hours in a humidified atmosphere with 5% CO2 at 37° C. Considering the penetration of cell membrane dye (CellMask™ Deep Red) and the working distance of objective lens, the inventors chose the spheroids with diameter of 90 to 110 µm with a cell-seeding density of 125 cells per well (see FIG. 17).

Figure 17:
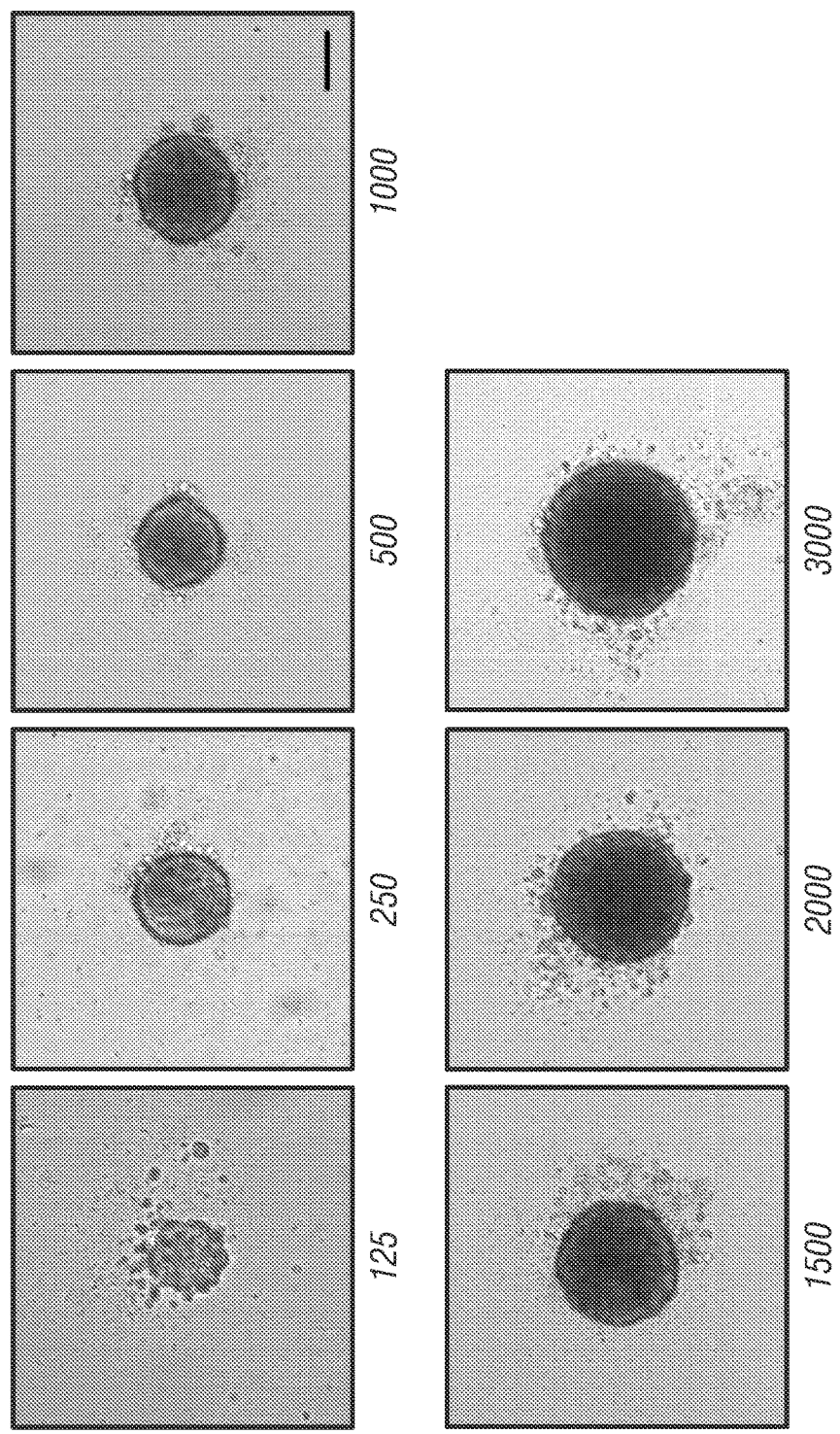
FIG. 17 shows data relating to spheroid formation and initiation protocol for A431 cells.

FIG. 17 shows spheroid formation and initiation protocol for A431 cells. Bright field imaging of MCTSs formed in liquid overlay from dissociated, exponentially growing A431 skin epidermoid carcinoma cells after a 96-hr initiation interval in agarose-coated 96-well microliter plates. The seeding density was between 125 and 3000 per well in 200 µl of serum-conditioned high glucose standard medium. The concentration to routinely and reproducibly obtain spheroids with a diameter of 90-110 µm is 125 cells per well. Scale bar is 100 µm.

Figure 18:
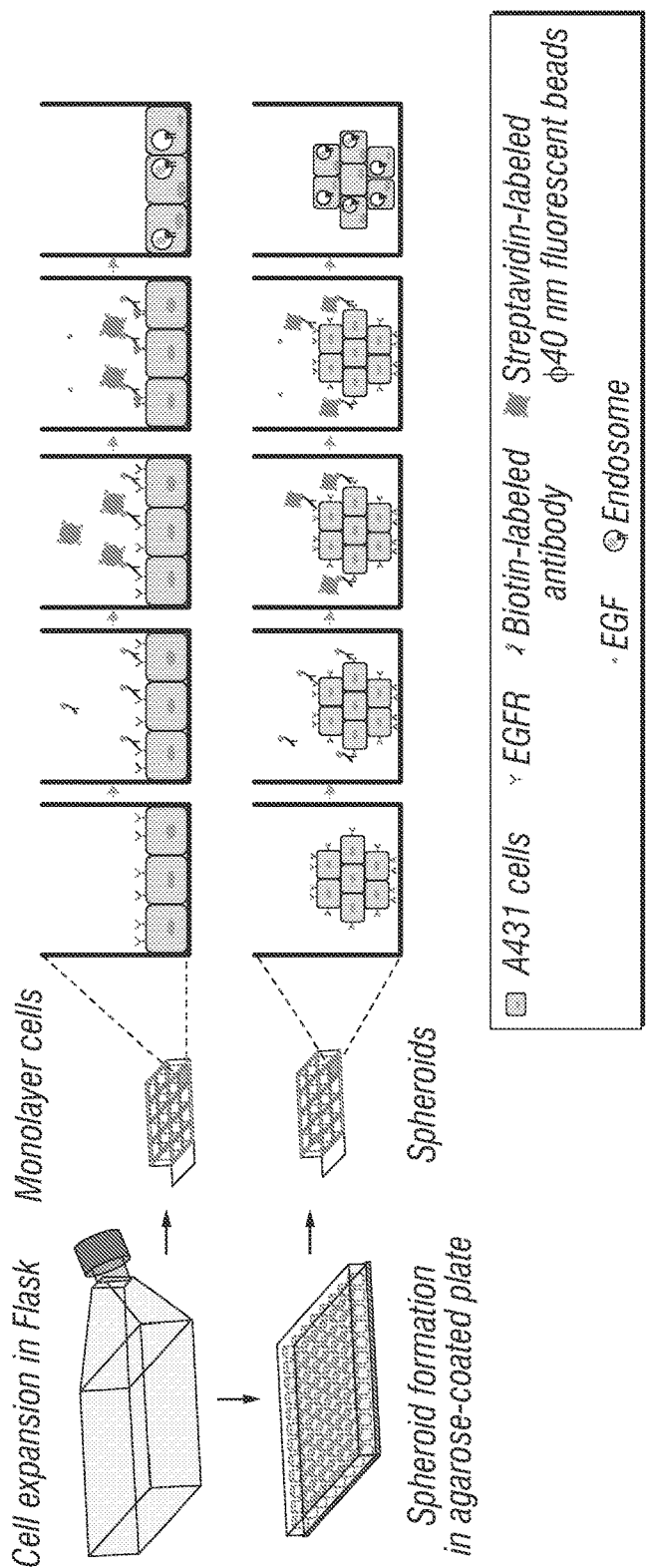
FIG. 18 shows a schematic of the preparation of samples for EGFR tracking.
Figure 19A:
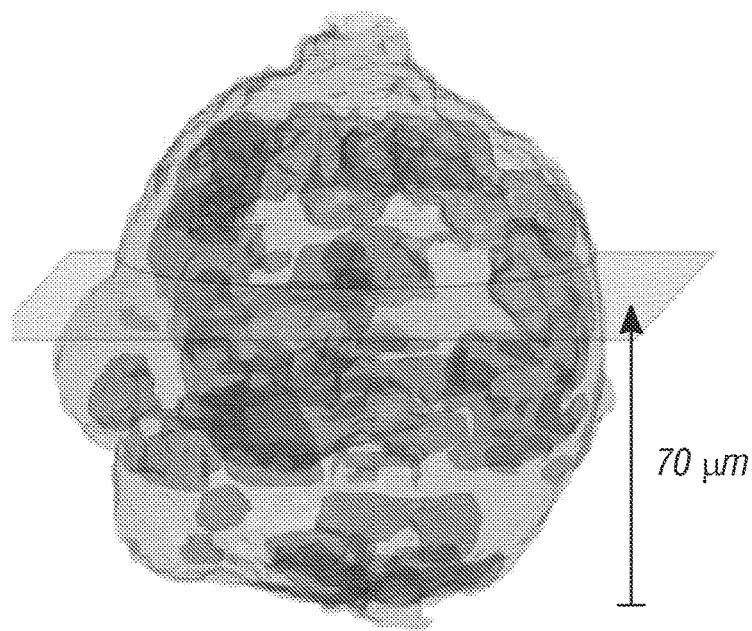
FIG. 19 shows data relating to deep single particle tracking of EGFR in spheroid model.
Figure 19B:
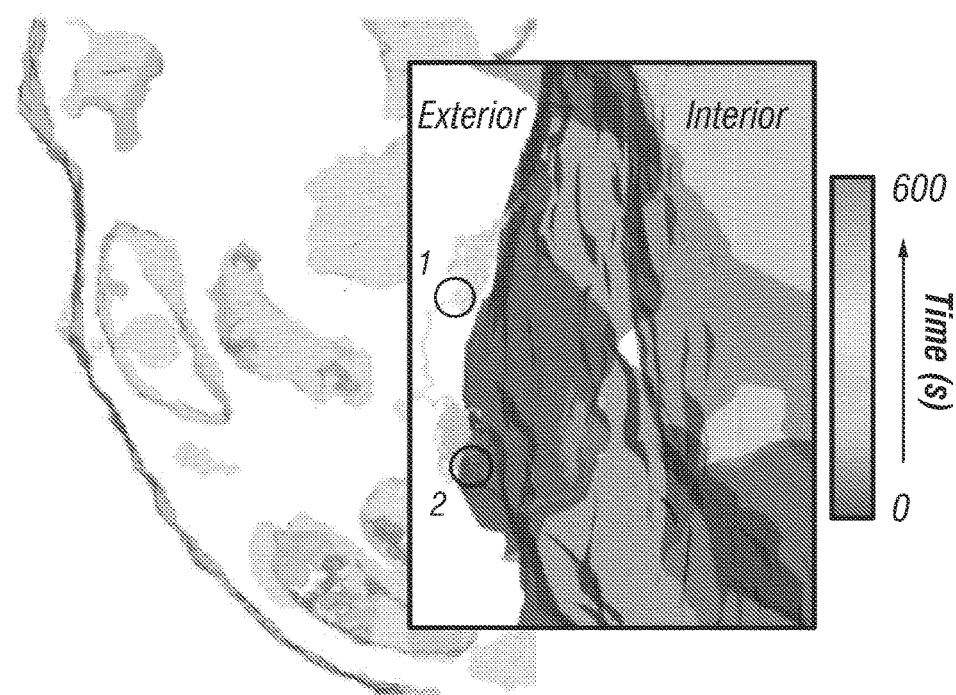
Figure 19C:
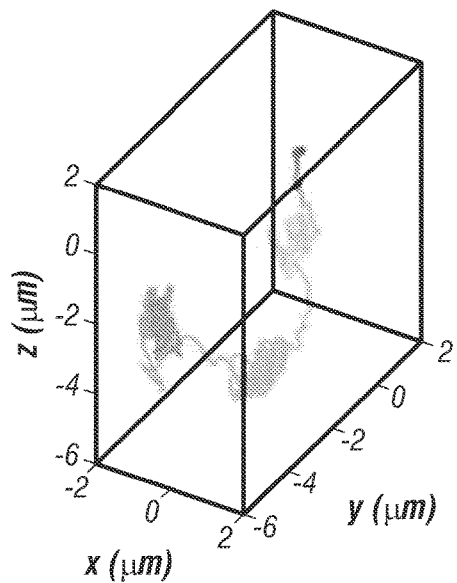
Figure 19D:
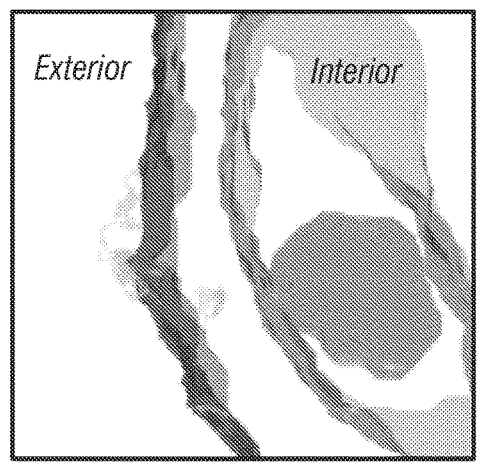
Figure 19E:
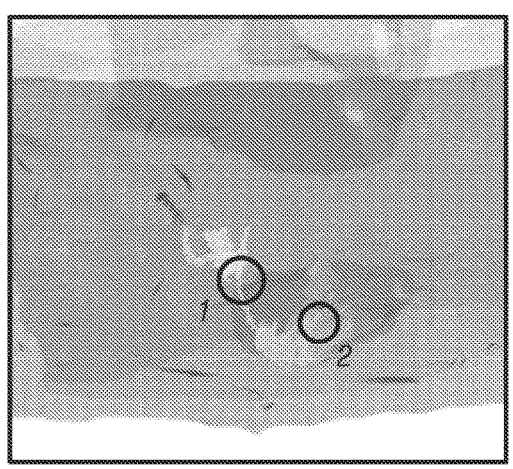
Figure 19F:
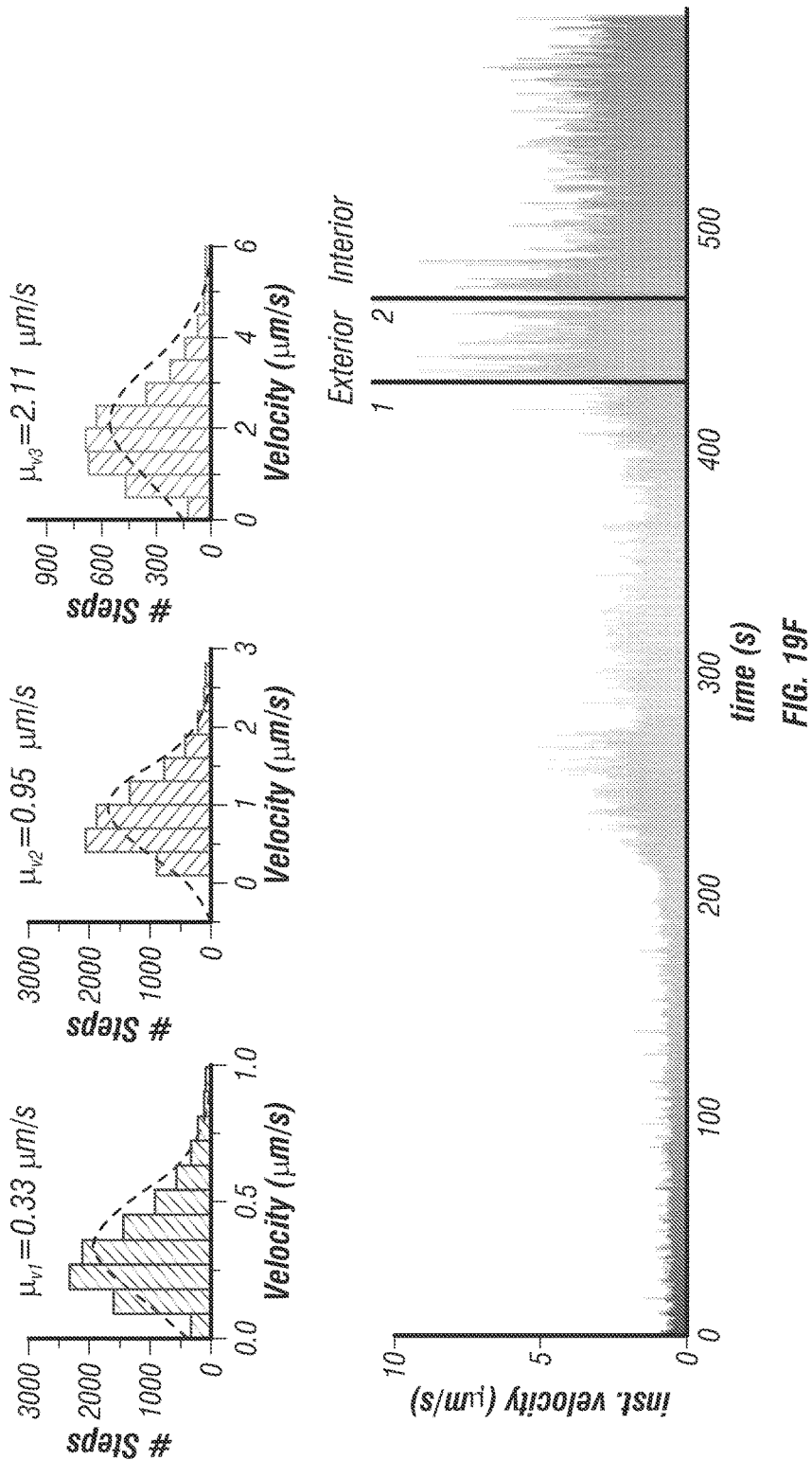

Both monolayer cells and spheroids were kept for additional 24 hours under serum-starvation condition before EGFR tracking. Plasma membrane was stained with CellMask™ and surface EGFRs were labeled with fluorescent nanoparticles (see FIG. 18). FIG. 18 shows the preparation of samples for EGFR tracking. A431 cells were expanded in flasks and the dissociated into single-cell suspension with trypsin treatment. For EGFR tracking in monolayer cells, the cells from suspension were directly seeded into chamber slides. The monolayer cells were stained with CellMask™ Deep Red and their EGFRs were recognized by antibodies and labeled with fluorescent nanoparticles. For spheroids, the suspended single cells were seeded into agarose-coated and incubated for 96 hours to form spheroids. After serum starvation, the spheroids were transferred to chamber slides for membrane staining and EGFR labeling.

Figure 21:
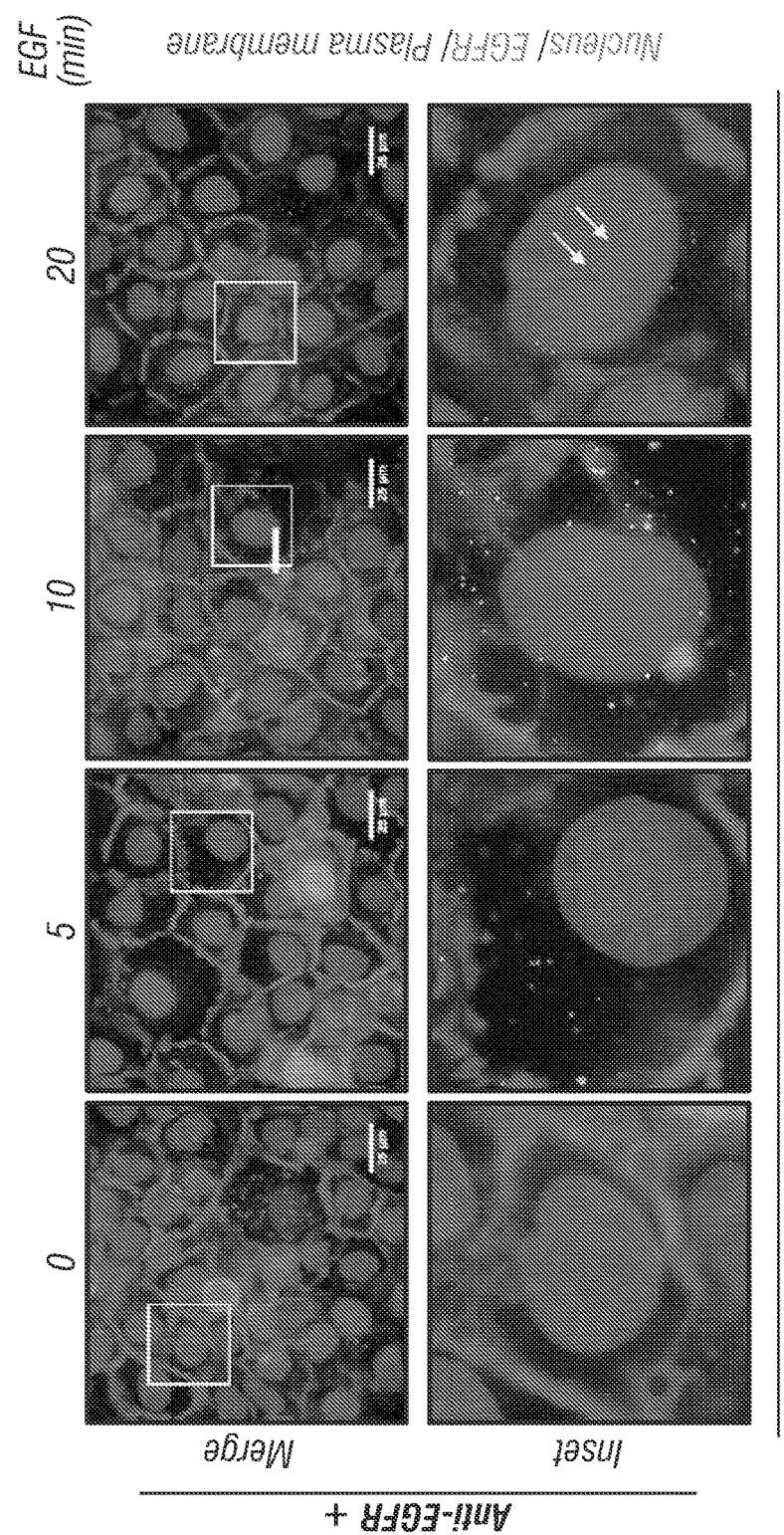
FIG. 21 shows data illustrating that EGF induces internalization of EGFR.
Figure 21:
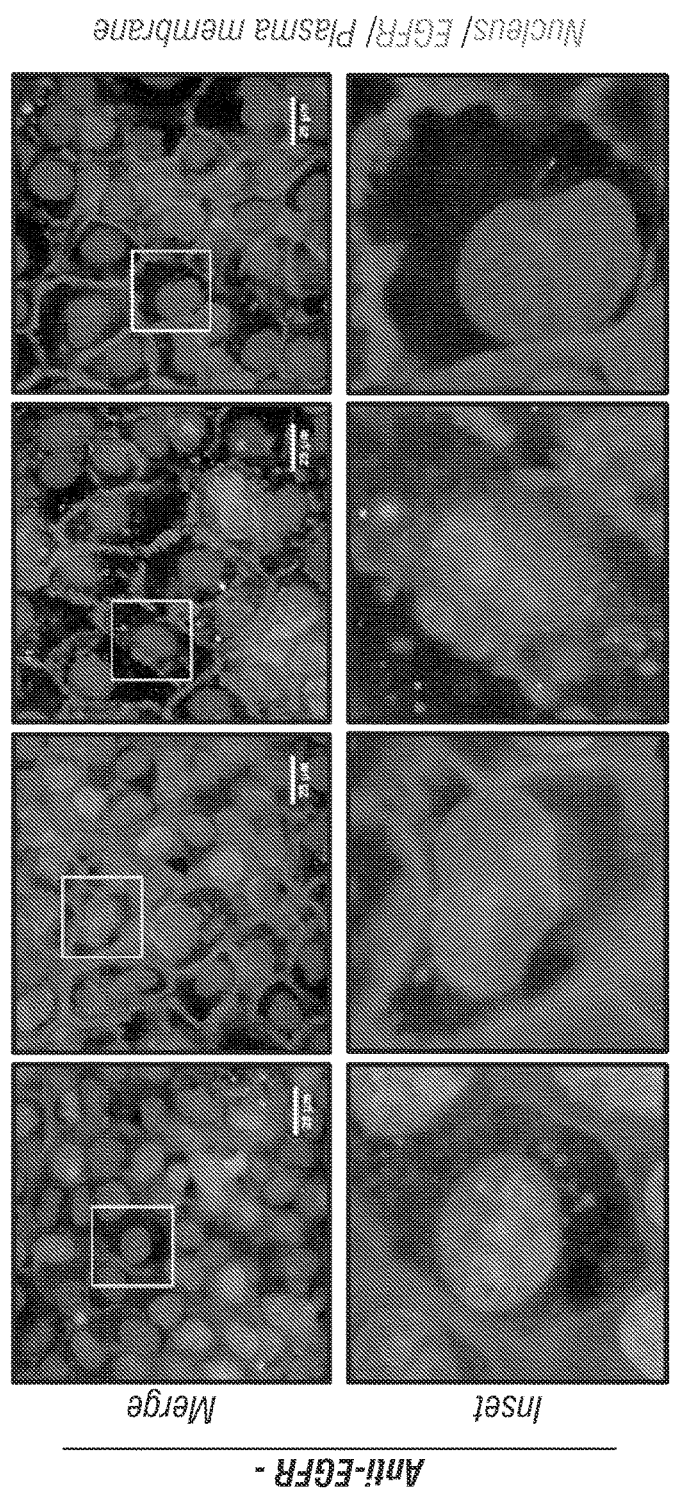
Figure 22A:
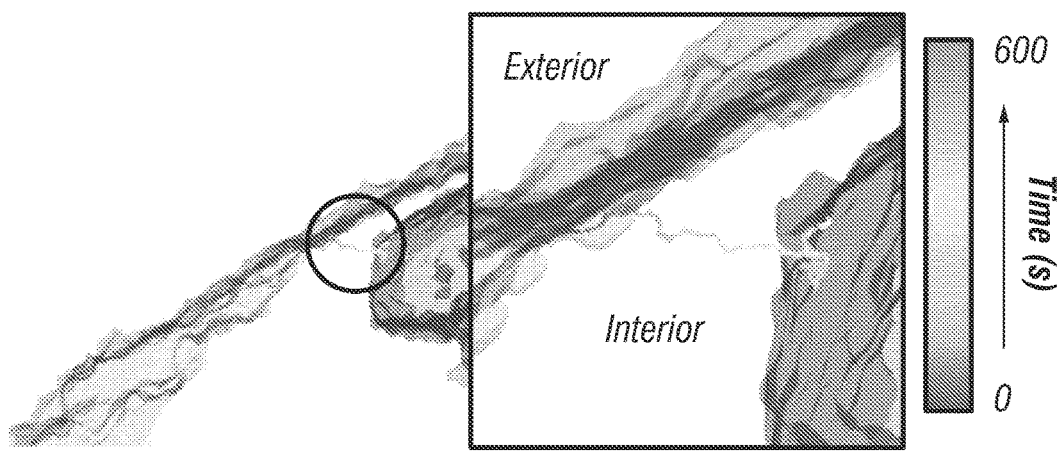
FIG. 22 shows data relating to intra-cellular transport in a spheroid model.
Figure 22B:
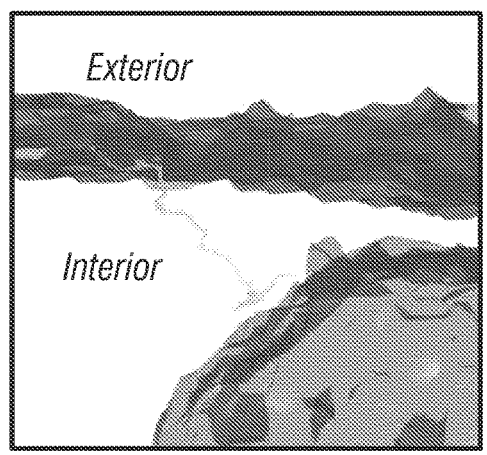
Figure 22C:
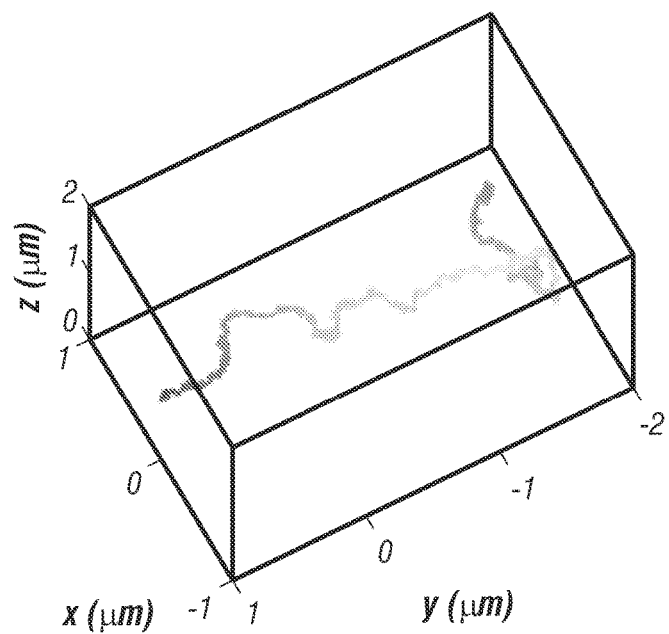
Figure 22D:
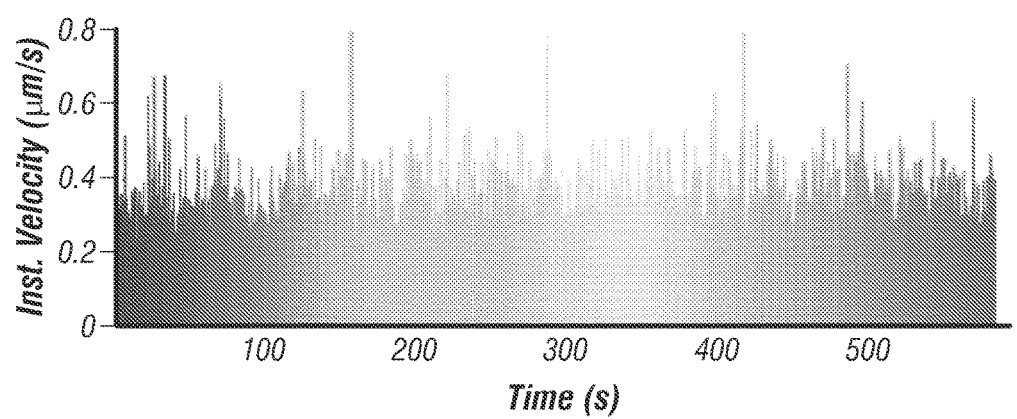

FIG. 21 shows EGF induces internalization of EGFR. As shown in this figure, monolayer A431 cells were exposed to serum-free media overnight, and then their EGFRs were recognized with biotin-conjugated anti-EGFR antibodies, and NeutrAvidin® conjugated red fluospheres (F8770, Life Technologies) bound to biotins to label EGFRs. In the control group, the inventors did not label EGFR with anti-EGFR antibodies. After labeling, cells were treated with EGF (20 ng/ml) for indicated time. The white arrows indicate nuclear translocation of EGFR. The boxed areas are shown in detail in the insets. Scale bar is 25 µm.

To label EGFRs with fluorescence, the cells were incubated with 1.5% BSA solution (1.5% bovine serum albumin, Cat. No. 57806) for 15 minutes at 37° C., and then EGFRs were labelled with biotinylated anti-EGFR antibodies (200 ng/ml in 1.5% BSA solution; Epidermal Growth Factor Receptor Ab-3, Cat. No. MS-311-B, Thermo Scientific) for 15 minutes at 37° C. The antibody solution was removed and cells were washed twice using PBS. The stock solution of . . . 40 nm fluorescent nanoparticles (FluoSpheres® NeutrAvidin®-Labeled Microspheres No. F8770, Life Technologies) was sonicated for 10 minutes and then diluted to 100 pM in DMEM. This solution was added into samples for 5 minutes at 37° C.

FIG. 19 discloses deep single particle tracking of EGFR in spheroid model, in particular an example EGFR entry pathway measured with 2P SPT 70 nm deep in a spheroid model. FIG. 19a discloses 3D Iso-contour of a 100 µm diameter spheroid taken with 2P LSM staining for plasma membrane (red) and nuceli (blue). The highlighted slice denotes the z-plane where the trajectory was measured. FIG. 19b shows close up 3D isocontour plot of a slice 70 µm deep into the spheroid taken with 2P LSM. (Inset: Close up view of the trajectory showing is location relative to the plasma membrane). The trajectory is 10 minutes long, color coded by time, with blue denoting the beginning. Points marked 1 and 2 are regions with an onset of high velocity. Point 2 denotes the point where the particle was most likely internalized due to large displacement (~1 µm) transverse to the membrane. FIG. 19c shows 3D Trajectory plot with no cell overlay. FIG. 19d shows a top view of the trajectory FIG. 19e. shows a side view of the trajectory FIG. 19f shows a velocity plot color coded by time showing a stepwise increase in instantaneous velocity over the course of 10 minutes. (Insets: Histograms of regions of the instantaneous velocity plot. The particle starts at 0.33 µm/s mean velocity from time 0-100 s, and accelerates to 2.11 µm/s from time 400 s-500 s.)

Figure 20A:
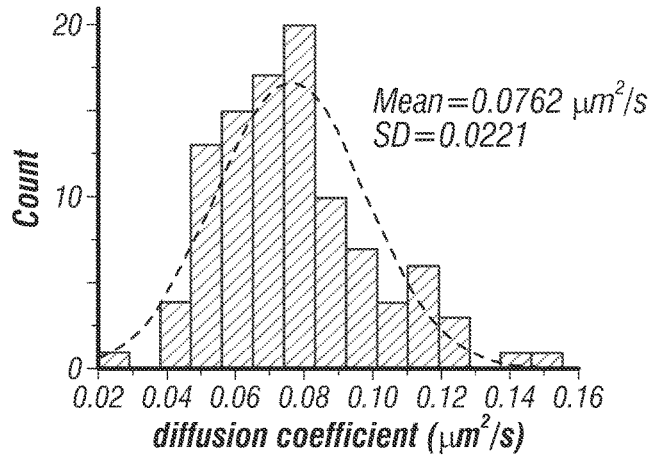
FIG. 20 shows data relating to free diffusion validation with glycerol titration.
Figure 20B:
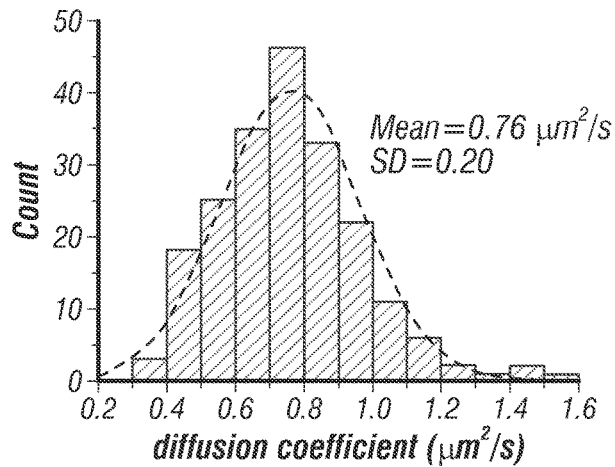
Figure 20C:
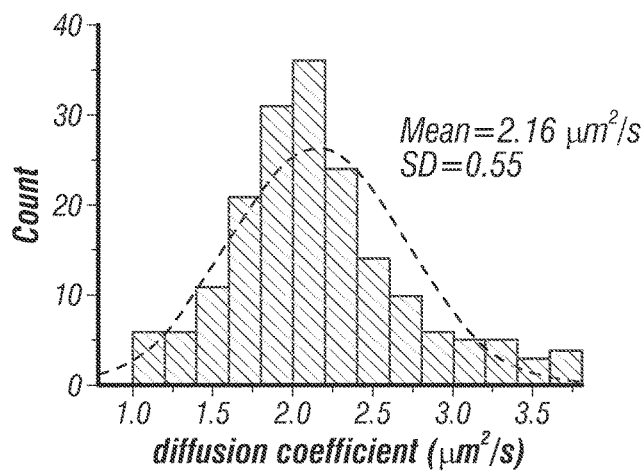
Figure 20D:
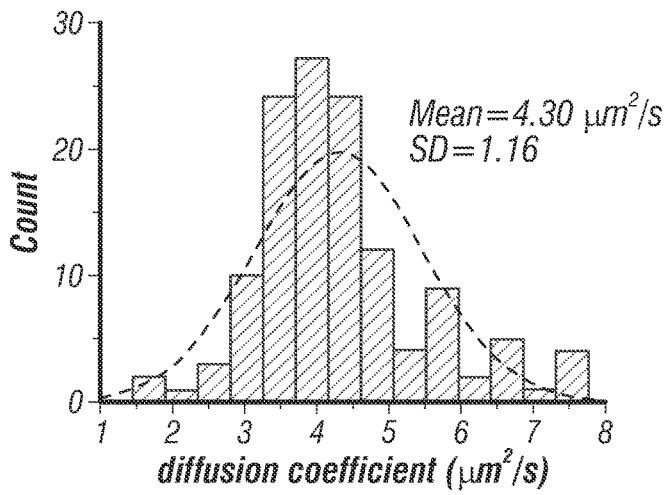
Figure 20E:
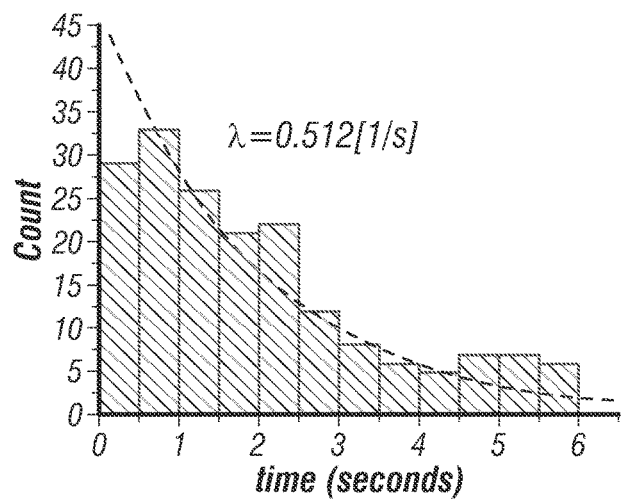
Figure 20F:
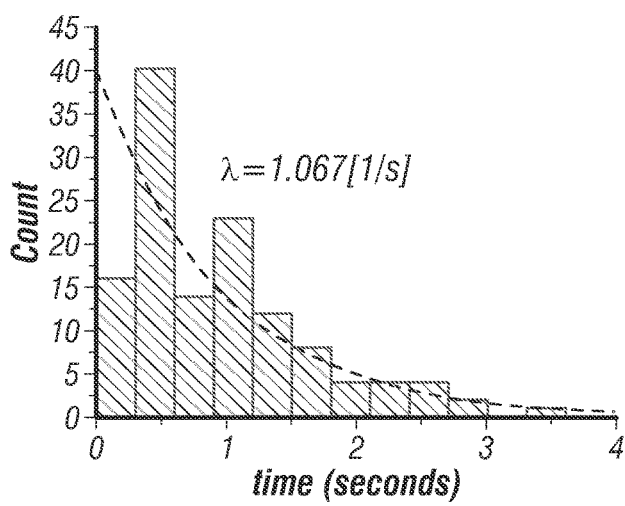

FIG. 22 shows intra-cellular transport in a spheroid model. In this figure, an additional EGF trajectory is taken in a spheroid model. This example trajectory shows slow diffusive transport in cytosol and interaction with the nucleus. FIG. 22A shows isocontour of the zoomed in image stack taken 90 µm deep in a spheroid with cell membrane (red) and nucleus (blue) are overlaid with the trajectory (black circle), (inset: zoomed view of the trajectory). The trajectory begins inside the cell close to the plasma membrane and ends at the nuclear membrane. FIG. 22b shows an additional close view of the trajectory from top down perspective. FIG. 22c shows a plot of the trajectory. FIG. 20d shows an instantaneous velocity plot over the 10 minute duration of the trajectory.

FIG. 20 shows free diffusion validation with glycerol titration. The system's capability to track particles under free diffusion was tested by observing mobile 100 nm diameter fluorescent beads in a range of different viscosities. The fluorescent beads were mixed with glycerol and water to achieve concentrations of 80% (FIG. 20a), 50% (FIG. 20b), 25% (FIG. 20c) and 0% (FIG. 20d) glycerol by weight. Particles were tracked for a duration of 10 seconds or until they were lost. Between 100 and 150 trajectories were taken at each data point. The diffusion coefficients are calculated by mean-squared-displacement analysis of the resulting trajectories. Histograms of the diffusion coefficient recorded from different viscosities (FIGS. 20a-d) all represented a normal distribution with central tendency that agreed well (within 1% at 21° C.) with the theoretical Stokes-Einstein relation. FIG. 20e shows a histogram of trajectory durations, with 25% glycerol mixture, which is found to follow an exponential distribution with a mean tracking duration of ~2 seconds. FIG. 20F shows a histogram of trajectory durations with 0% glycerol and 100% water mixture. With glycerol mixtures above 25% wt. the target locking was stable and more than 99% of the trajectories were recorded up until the software imposed time limit of 10 seconds.

FIG. 21 shows EGF induces internalization of EGFR. Monolayer A431 cells were exposed to serum-free media overnight, and then their EGFRs were recognized with biotin-conjugated anti-EGFR antibodies, and NeutrAvidin® conjugated red fluospheres (F8770, Life Technologies) bound to biotins to label EGFRs. In the control group, the inventors didn't label EGFR with anti-EGFR antibodies. After labeling, cells were treated with EGF (20 ng/ml) for indicated time. The white arrows indicate nuclear translocation of EGFR. The boxed areas are shown in detail in the insets. Scale bar is 25 μm.

FIG. 22 illustrates intra-cellular transport in a spheroid model, specifically an additional EGF trajectory taken in a spheroid model. This example trajectory shows slow diffusive transport in cytosol and interaction with the nucleus. FIG. 22a shows isocontour of the zoomed in image stack taken 90 μm deep in a spheroid with cell membrane (red) and nucleus (blue) are overlaid with the trajectory (black circle), (inset: zoomed view of the trajectory). The trajectory begins inside the cell close to the plasma membrane and ends at the nuclear membrane. FIG. 22b shows additional close view of the trajectory from top down perspective. FIG. 22c shows a plot of the trajectory. FIG. 22d shows instantaneous velocity plot over the 10 minute duration of the trajectory.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

1. Kusurni et al., *Nat. Chem. Biol.* 10: 524-32 (2014).
2. Levi et al., *Biophys. J.*, 88:2919-78, 2005.
3. Cang et al., *Opt. Lett.*, 32:2729-31, 2007.
4. Yildiz et al., *Science,* 300:2061-5, 2003.
5. Gelles et al., *Nature,* 331:450-453, 1988,
6. Fujiwara et al., *J. Cell Biol.*, 157:1071-81, 2002.
7. Dahan et al., *Science,* 302:442-5, 2003.
8. Andrews et al., *Nat. Cell Biol.*, 10:955-63, 2008.
9. Park et al., *Science,* 343:422-4, 2014.
10. Shav-Tal et al., *Science,* 304:1797-800, 2004.
11. Huang et al., *Nat. Methods,* 5:1047-1052, 2008.
12. Arhel, N. et al., *Nat. Methods,* 3: 817-24, 2006.
13. Wirtz, *Annu. Rev. Biophys.*, 38:301-26, 2009.
14. Welsher and Yang, *Nat. Nanotechnol,* 9:198-203, 2014.
15. Wells, N. P. et al, *Nano Lett,* 10: 4732-7, 2010.
16. Sahl et al., *Proc. Natl. Acad. Sci.*, 107:6829-6834, 2010.
17. Thompson et al., *Nano Lett.*, 10:211-8, 2010.
18. Van den Broek et al., *Nano Lett,* 13:980-6, 2013.
19. Cang et al., *Chem. Phys. Lett.*, 457:285-291, 2008.
20. Helmchen and Denk, *Nat. Methods,* 2:932-40, 2005.
21. McHale et al., *Nano Lett.*, 7:3535-9, 2007.
22. Kim et al., *Opt. Express,* 15:11658-78, 2007.
23. Liu et al., *Proc. SPIE,* 8950:1-9, 2014.
24. ii et: al., *Nat Methods,* 1-6, 2008.
25. Cheng e *Nat. Methods,* 8:139-42, 2011.
26. Dertinger et al., *Chemphyschem,* 8:433-43, 2007.
27. Germann and Davis, *Opt. Express,* 22:9830-9834, 2014.
28. Lee et al., *Proc. Natl. Acad. Sci. U.S.A.*, 109:6531-6, 2012.
29. Pyenta et al., *J. Phys. Chem. A,* 107:8310-8318, 2003.
30. Griffin et al., *Cell,* 146:955-68, 2011.
31. Hayakawa et al., *Phys. Rev. Lett.*, 103: 043903, 2009.
32. De Bruin et al. Cellular dynamics of EGF receptor-targeted synthetic viruses. *Mol. Ther.* 15, 1297-305 (2007).
33. Spille et al., *Opt. Express,* 20:19697-707, 2012.
34. Wang and Moerner, *Nat. Methods,* 11:555-8, 2014.
35. Juette et al., *Appl. Phys. Lett.*, 102:173702, 2013.
36. Myong et al., *Nature* 437:1321-5, 2005.
37. Gebhardt et al., *Nat. Methods,* 10:421-6, 2013.
38. Ulbrich and Isacoff, *Nat. Methods,* 4:319-21, 2007
39. Friedrich et al., *Nat. Protoc.*, 4:309-24, 2009.

The invention claimed is:

1. A method of tracking a single particle, the method comprising:
   separating an input light beam emitted from a light source into a plurality of excitation light beams that are spatially and temporally offset;
   illuminating a single particle with the plurality of light beams that are spatially and temporally offset;
   detecting fluorescence emitted from the single particle; and
   processing photon histogram data resulting from the illumination of the single particle by the plurality of excitation light beams that are spatially and temporally offset to determine a location of the single particle at specific time, wherein processing photon histogram data comprises:
      counting and correlating signal photons to a reference clock;
      extracting count values from a photon histogram;
      selecting a plurality of windows from the photon histogram;
      obtaining a time gate value from an average value for each window of the photon histogram;

applying a fluorescence correction factor to the time gate value to generate a corrected time gate value for each window of the photon histogram;
subtracting dark count values from the corrected time gate value for each window of the photon histogram;
calculating error signals from normalized time window differences;
applying proportional control gain values to the error signals; and
performing geometric transform to switch from point-spread function error vectors to galvanic space error vectors.

2. The method of claim 1 wherein the input light beam emitted from the light source is separated into the plurality of excitation light beams via passive beam splitters.

3. The method of claim 1 wherein:
the plurality of excitation light beams that are spatially and temporally offset comprises a first light beam and a second light beam; and
the first light beam is temporally offset between 1 and 20 nanoseconds from the second light beam.

4. The method of claim 3 wherein:
the plurality of excitation light beams that are spatially and temporally offset comprises a third light beam and a fourth light beam; and
the third light beam is temporally offset between 1 and 20 nanoseconds from the fourth light beam.

5. The method of claim 4 wherein the third excitation beam is temporally offset between 1 and 20 nanoseconds from the second excitation beam.

6. The method of claim 1 wherein:
the plurality of excitation light beams that are spatially and temporally offset comprises a first light beam and a second light beam; and
the first light beam is temporally offset between 1 and 10 nanoseconds from the second light beam.

* * * * *